United States Patent
Reunanen

(10) Patent No.: US 11,908,138 B2
(45) Date of Patent: *Feb. 20, 2024

(54) PROCESSING PATHOLOGY IMAGES

(71) Applicant: AIFORIA TECHNOLOGIES OYJ, Helsinki (FI)

(72) Inventor: Juha Reunanen, Helsinki (FI)

(73) Assignee: AIFORIA TECHNOLOGIES OYJ, Helsinki (FI)

( * ) Notice: Subject to any disclaimer, the term of this patent is extended or adjusted under 35 U.S.C. 154(b) by 0 days.

This patent is subject to a terminal disclaimer.

(21) Appl. No.: 18/341,940

(22) Filed: Jun. 27, 2023

(65) Prior Publication Data

US 2023/0342930 A1    Oct. 26, 2023

Related U.S. Application Data

(63) Continuation of application No. 18/067,507, filed on Dec. 16, 2022, now Pat. No. 11,727,566, which is a (Continued)

(51) Int. Cl.
   *G06T 7/00* (2017.01)
   *G06T 3/40* (2006.01)
   *G16H 30/20* (2018.01)

(52) U.S. Cl.
   CPC .......... *G06T 7/0012* (2013.01); *G06T 3/4046* (2013.01); *G06T 2207/10056* (2013.01);
   (Continued)

(58) Field of Classification Search
   None
   See application file for complete search history.

(56) References Cited

U.S. PATENT DOCUMENTS

| 5,638,498 A | 6/1997 | Tyler et al. |
| 7,139,433 B2 | 11/2006 | Li |

(Continued)

OTHER PUBLICATIONS

"Deep Zoom," Wikipedia [online], last edited Jan. 27, 2021 [retrieved on Feb. 10, 2021]. Retrieved from <url: https://en.wikipedia.org/wiki/Deep_Zoom>, 4 pages.

(Continued)

*Primary Examiner* — Samah A Beg
(74) *Attorney, Agent, or Firm* — Leber IP Law; Celia H. Leber

(57) ABSTRACT

A method of facilitating processing of pathology images involves receiving pathology image data representing a pathology image having a plurality of image regions, wherein the pathology image data includes, for each of the plurality of image regions, a respective plurality of representations of the image region including a first representation and a second representation, the second representation having a smaller data size than the first representation. The method involves, for each of the plurality of image regions: determining, based at least in part on the first representation of the image region, a first set of image properties, determining whether the first set of image properties meets first image property criteria, and, if the first set of image properties meets the first image property criteria, producing signals for causing the second representation to be used in place of the first representation. Other methods, systems, and computer-readable media are disclosed.

23 Claims, 12 Drawing Sheets

Related U.S. Application Data continuation of application No. 17/749,917, filed on May 20, 2022, now Pat. No. 11,562,485, which is a continuation of application No. 17/410,465, filed on Aug. 24, 2021, now Pat. No. 11,373,306.

(60) Provisional application No. 63/221,109, filed on Jul. 13, 2021.

(52) U.S. Cl.
CPC .............. *G06T 2207/20081* (2013.01); *G06T 2207/20084* (2013.01); *G16H 30/20* (2018.01)

(56) References Cited

U.S. PATENT DOCUMENTS

| | | | |
|---|---|---|---|
| 9,280,836 B1 | 3/2016 | Craik | |
| 9,439,565 B1* | 9/2016 | Chai | G16H 30/20 |
| 2014/0293307 A1 | 10/2014 | Tamada | |
| 2016/0247310 A1* | 8/2016 | Hui | G06T 1/20 |
| 2018/0302625 A1 | 10/2018 | Gadelrab et al. | |
| 2020/0014740 A1 | 1/2020 | Chao et al. | |

OTHER PUBLICATIONS

Adelson, Edward; et al., "Image Data Compression With the Laplacian Pyramid," Reprinted from Proceedings of the Pattern Recognition and Information Processing Conference, IEEE, Dallas, Texas, 1981, pp. 218-222.

Calkins, Charles; "Large Image Display With Seadragon Ajax," Object Computing.com, Oct. 2011 [online] [retrieved on Feb. 4, 2021]. Retrieved from <url: https://objectcomputing.com/resources/publications/sett/october-2011-large-image-display-with-seadragon-ajax>, 37 pages.

"Missing tiles at certain zoom level for certain parts on my own tile server," OpenStreetMapp, Sep. 10, 2015 [online] [retrieved on Feb. 4, 2021]. Retrieved from <url: https://help.openstreetmap.org/questions/45114/missing-tiles-at-certain-zoom-level-for-certain-parts-on-my-own-tile-server?page=1&focusedAnswerId=45176#45176>, 2 pages.

Khushi, Matloob; et al., "Open source tools for management and archiving of digital microscopy data to allow integration with patient pathology and treatment information," Diagnostic Pathology, vol. 8, Article 22, published Feb. 12, 2013, 7 pages.

Leroux, C.; "Neural network—Let's try to demystify all this a little bit (3)—Application to images," Aspexit.com [online], posted Apr. 12, 2019, [retrieved on Sep. 29, 2021]. Retrieved from <url: https://www.aspexit.com/neural-network-lets-try-to-demystify-all-this-a-little-bit-3-application-to-images/>, 10 pages.

"An open-source, web-based viewer for high-resolution zoomable images," OpenSeadragon [online], [retrieved on Sep. 29, 2021]. Retrieved from <url:https://openseadragon.github.io/> and <url:https://github.com/openseadragon/openseadragon/blob/master/src/tiledimage.js>, 54 pages.

International Patent Application No. PCT/FI2022/050439, International Search Report and Written Opinion dated Oct. 10, 2022, 12 pages.

\* cited by examiner

PROCESSING PATHOLOGY IMAGES

RELATED APPLICATION

This application is a continuation of U.S. patent application Ser. No. 18/067,507 filed Dec. 16, 2022, which is a continuation of U.S. patent application Ser. No. 17/749,917, filed May 20, 2022, now U.S. Pat. No. 11,562,485, granted Jan. 24, 2023, which is a continuation of U.S. patent application Ser. No. 17/410,465, filed Aug. 24, 2021, now U.S. Pat. No. 11,373,306, granted Jun. 28, 2022, which claims the benefit of U.S. Provisional Application No. 63/221,109 entitled "processing pathology images", filed on Jul. 13, 2021, the entire contents of which are hereby incorporated by reference.

BACKGROUND

1. Field

Embodiments of the present disclosure relate to processing pathology images and more particularly to facilitating processing of pathology images.

2. Description of Related Art

Image analysis is playing an increasing role globally in pathology and various medical diagnostic applications. Image analysis may involve processing and/or manipulating pathology images, which in some cases may be extremely large and/or difficult to process and/or manipulate. In order to process and/or manipulate pathology images, some known systems may be slow, costly and/or inefficient.

SUMMARY

In accordance with various embodiments, there is provided a method of facilitating processing of pathology images. The method involves receiving pathology image data representing a pathology image having a plurality of image regions, wherein the pathology image data includes, for each of the plurality of image regions, a respective plurality of representations of the image region including a first representation and a second representation, the second representation having a smaller data size than the first representation. The method involves, for each of the plurality of image regions: determining, based at least in part on the first representation of the image region, a first set of image properties, determining whether the first set of image properties meets first image property criteria, and, if the first set of image properties meets the first image property criteria, producing signals for causing the second representation to be used in place of the first representation.

The second representation may have a pixel width smaller than a pixel width of the first representation and the second representation may have a pixel height smaller than a pixel height of the first representation.

For each of the plurality of image regions, the first set of image properties may represent a difference between the first and second representations of the image region.

For each of the plurality of image regions, determining the first set of image properties may involve determining based on at least the first and second representations, a first image difference representing the difference between the first and second representations of the image region.

For each of the plurality of image regions, determining the first image difference may involve upscaling the second representation of the image region to generate a first upscaled representation of the image region, the first upscaled representation of the image region having the same pixel dimensions as the first representation of the image region, and, for each pixel position in the first representation and the first upscaled representation, determining a pixel value difference between respective pixels of the first representation and the first upscaled representation.

For each of the plurality of image regions, determining the first image difference may involve determining from the pixel value differences, a first maximum pixel value difference, and determining whether the first set of image properties meets the first image property criteria may involve comparing the first maximum pixel value difference with a first maximum pixel difference threshold.

For each of the plurality of image regions, determining the first image difference may involve determining from the pixel value differences, an extreme negative pixel value difference, and determining from the pixel value differences, an extreme positive pixel value difference. For each of the plurality of image regions, determining whether the first set of image properties meets the first image property criteria may involve comparing the extreme negative pixel value difference with an extreme negative pixel difference threshold, and comparing the extreme positive pixel value difference with an extreme positive pixel difference threshold, the extreme positive pixel difference threshold being different from the extreme negative pixel difference threshold.

For each pixel position in the first representation and the first upscaled representation, determining the pixel value difference may involve scaling the pixel value difference by a pixel value scaling factor, the pixel value scaling factor based at least in part on an overall pixel value intensity of the first representation.

For each of the plurality of image regions, the plurality of representations of the image region may include a third representation, the third representation having a smaller data size than the second representation. Determining whether the first set of image properties meets the first image property criteria may involve determining, based at least in part on the second representation of the image region, a second set of image properties, determining whether the second set of image properties meets second image property criteria, and, if the second set of image properties meets the second image property criteria, producing signals for causing the third representation to be used in place of the first representation.

For each of the plurality of image regions, determining the second set of image properties may involve determining based on at least the second and third representations, a second image difference representing a difference between the second and third representations of the image region. For each of the plurality of image regions, determining the second image difference may involve upscaling the third representation of the image region to generate a second upscaled representation of the image region, the second upscaled representation of the image region having the same pixel dimensions as the second representation of the image region, for each pixel position in the second representation and the second upscaled representation, determining a second pixel value difference between respective pixels of the second representation and the second upscaled representation, and determining from the second pixel value differences, a second maximum pixel value difference. Determining whether the second set of image properties meets the second image property criteria may involve comparing the second maximum pixel value difference with a second maximum pixel difference threshold, wherein the second maximum pixel difference threshold has a lower magnitude than the first maximum pixel difference threshold.

Producing signals for causing the second representation to be used in place of the first representation may involve producing signals for causing the second representation to be displayed by at least one display in place of the first representation.

The method may involve receiving a request for the first representation. Producing signals for causing the second representation to be used in place of the first representation may involve producing signals for causing the second representation to be provided in response to the request for the first representation.

For each of the plurality of image regions, determining the first set of image properties may involve inputting at least the first representation of the image region into a machine learning model to cause the machine learning model to generate at least one machine learning model image property.

The machine learning model may include a convolutional neural network.

The method may involve, for each of the plurality of image regions, whether the first set of image properties meets or does not meet the first image property criteria, causing the second representation to be stored such that the second representation is configured to be provided when requested.

Producing signals for causing the second representation to be used in place of the first representation may involve producing signals identifying the first representation as replaceable by the second representation.

Producing signals identifying the first representation as replaceable by the second representation may involve including an identifier of the first representation in a replaceable first representation record.

The replaceable first representation record may include an identifying image.

The identifying image may include a binary image.

In accordance with various embodiments, there is provided a system for facilitating processing of pathology images, the system including at least one processor configured to perform any of the above methods.

In accordance with various embodiments, there is provided a non-transitory computer-readable medium having stored thereon codes that when executed by at least one processor cause the at least one processor to perform any of the above methods.

In accordance with various embodiments, there is provided a system for facilitating processing of pathology images, the system including provisions for receiving pathology image data representing a pathology image having a plurality of image regions, wherein the pathology image data includes, for each of the plurality of image regions, a respective plurality of representations of the image region including a first representation and a second representation, the second representation having a smaller data size than the first representation, provisions for, for each of the plurality of image regions, determining, based at least in part on the first representation of the image region, a first set of image properties and determining whether the first set of image properties meets first image property criteria, and provisions for, if the first set of image properties meets the first image property criteria, producing signals for causing the second representation to be used in place of the first representation.

Other aspects and features of embodiments of the present disclosure will become apparent to those ordinarily skilled in the art upon review of the following description of specific embodiments of the present disclosure in conjunction with the accompanying figures.

BRIEF DESCRIPTION OF THE DRAWINGS

In drawings which illustrate embodiments of the present disclosure.

DETAILED DESCRIPTION

Figure 1:
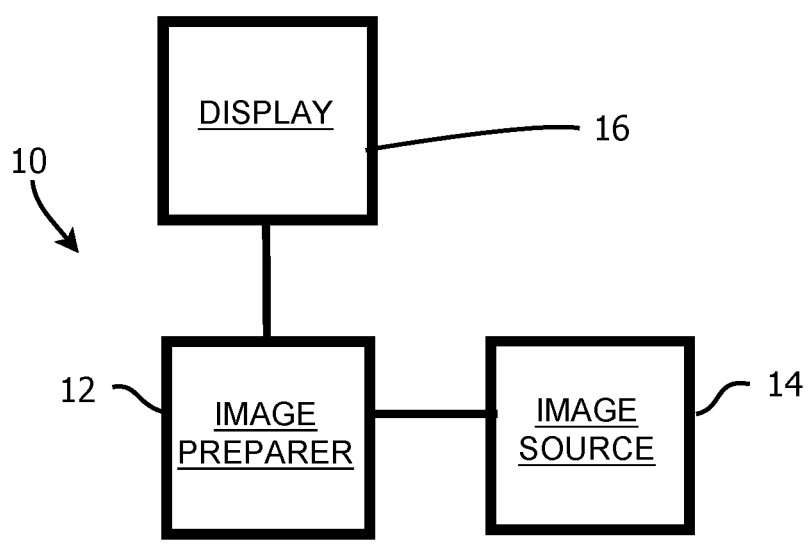
FIG. 1 is a schematic view of a system for facilitating processing of pathology images, according to various embodiments.

Referring to FIG. 1, there is provided a system 10 for facilitating processing of pathology images in accordance with various embodiments. The system 10 includes an image preparer 12 in communication with an image source 14. In some embodiments, the system includes a display 16 in communication with the image preparer 12. In various embodiments, the system 10 may facilitate fast, low cost, and/or efficient processing and/or manipulation of pathology images.

Figure 2:
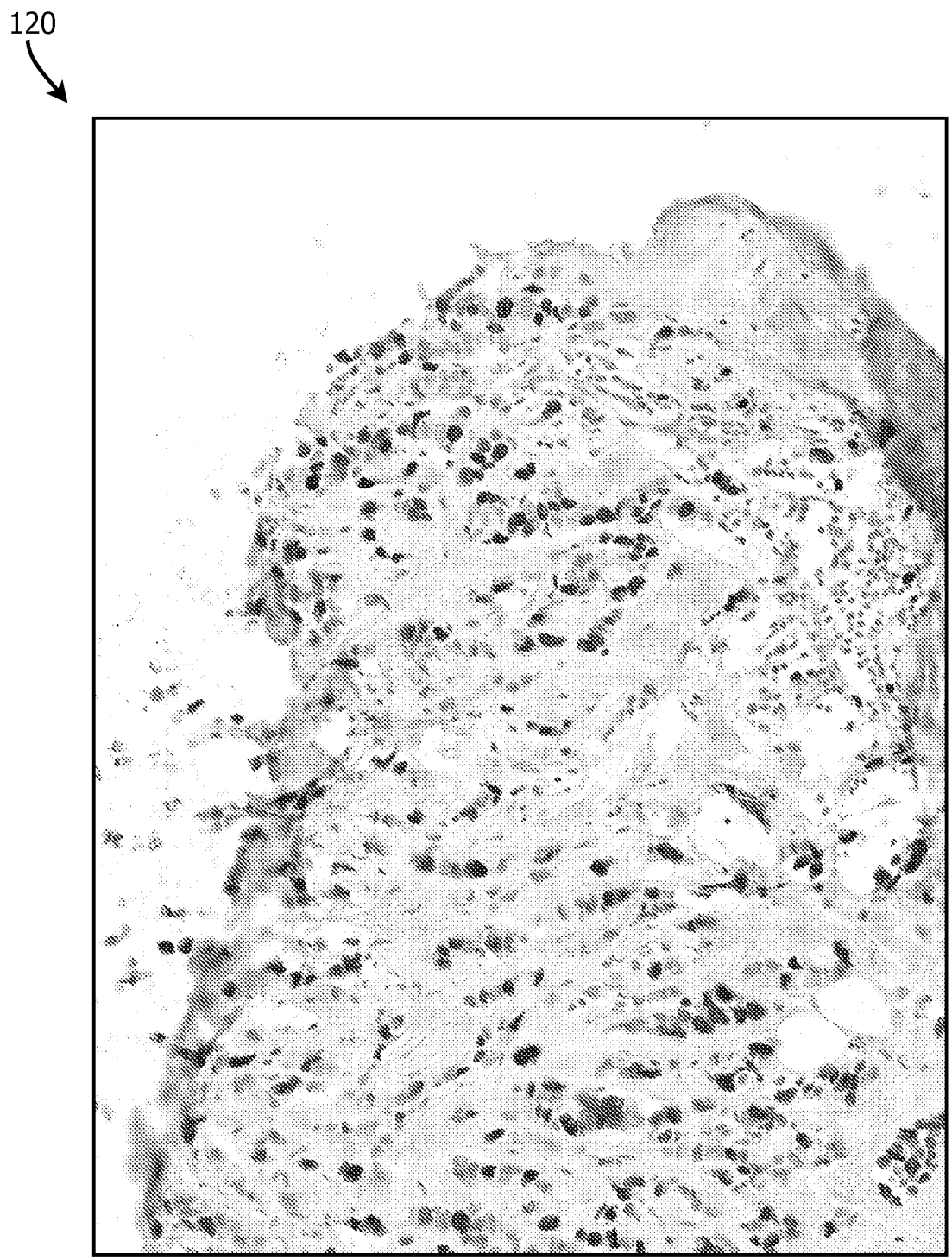
FIG. 2 is a representation of a pathology image that may be used in the system shown in FIG. 1, in accordance with various embodiments.

In various embodiments, the image preparer 12 may be configured to receive pathology image data representing a pathology image 120 shown in FIG. 2. For example, in some embodiments, the image preparer 12 may receive the pathology image data from the image source 14. In various embodiments, the image source 14 may have previously received and stored the pathology image data for analysis. In some embodiments, the image source 14 may include a picture archiving and communication system (PACS), for example. In some embodiments, the image preparer 12 may be configured to provide regular PACS functionality and the image source 14 may include a slide scanner, for example.

In some embodiments, the pathology image 120 shown in FIG. 2 may represent a microscope image of patient tissue that is to be analyzed, such as by machine and/or human analysis for pathology. In various embodiments, the image preparer 12 may be configured to process and/or prepare the pathology image data, to generate updated image data that may have improved compression and/or be well suited for display or processing, while preserving features that may be needed to perform image analysis for pathology. For example, in some embodiments, the image preparer 12 may be configured to improve and/or optimize storage and representation of the pathology image 120, such that it can be processed and/or displayed more quickly and/or with lower storage space requirements.

In some embodiments, the image preparer 12 may be configured to produce signals representing updated pathology image data for causing the updated pathology image data to be used for display and/or further processing. For example, in some embodiments, the image preparer 12 may be configured to cause the updated pathology image data to be stored by the image source 14 and the image preparer 12 or another device may be configured to cause the updated pathology image data to be displayed by the display 16.

Referring to FIG. 2, in some embodiments, the pathology image 120 may include a plurality of image regions and the pathology image data may include, for each of the image regions, a respective plurality of representations of the image region including a first representation and a second representation, the second representation having a smaller data size than the first representation. For example, in some embodiments, the pathology image data received from the image source 14 may define an image pyramid representing the pathology image 120 shown in FIG. 2.

Figure 3:
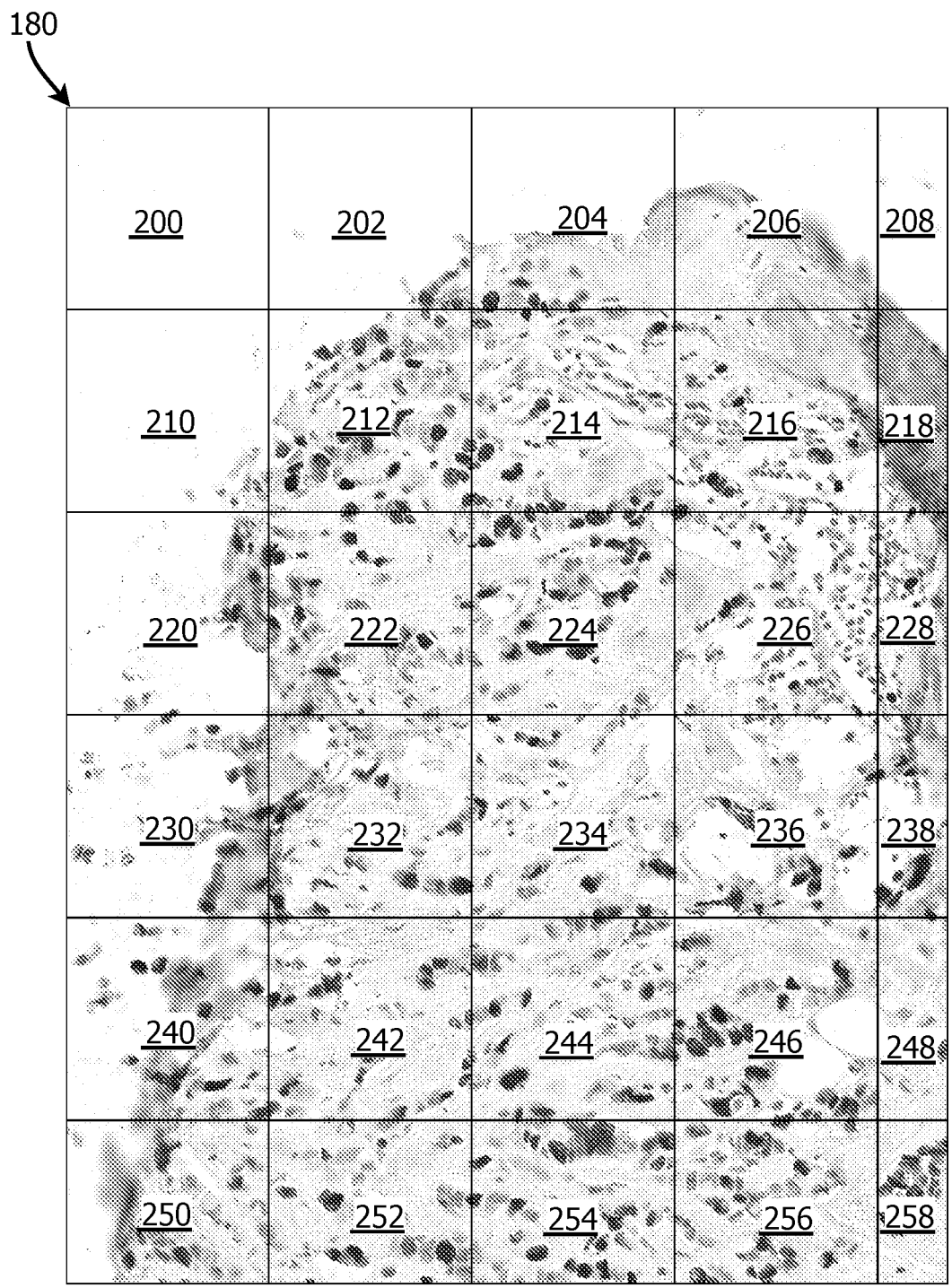
FIG. 3 is a representation of first level image regions of the pathology image shown in FIG. 2, in accordance with various embodiments.

In some embodiments, the pathology image 120 shown in FIG. 2 may be separable into a tiled grid 180 of respective first level image regions 200-258, as shown in FIG. 3. In some embodiments, the pathology image data received by the image preparer 12 may include respective first level image files or records or representations thereof (which may be implemented as identified portions or views of the pathology image 120, for example) representing the first level image regions 200-258, the first level image files each having, for example, a pixel width of up to 512 and a pixel height of up to 512. For example, in some embodiments, each of the first level image regions 200-206, 210-216, 220-226, 230-236, and 240-246 may have a pixel width of 512 and a pixel height of 512. In some embodiments, the first level image regions 208, 218, 228, 238, 248, and 250-258 may be on the edge of the pathology image 120 and so the first level image files representing these regions may have pixel widths and heights of less than 512 pixels, though the pixel density may be the same as in the other first level image files.

Figure 4:
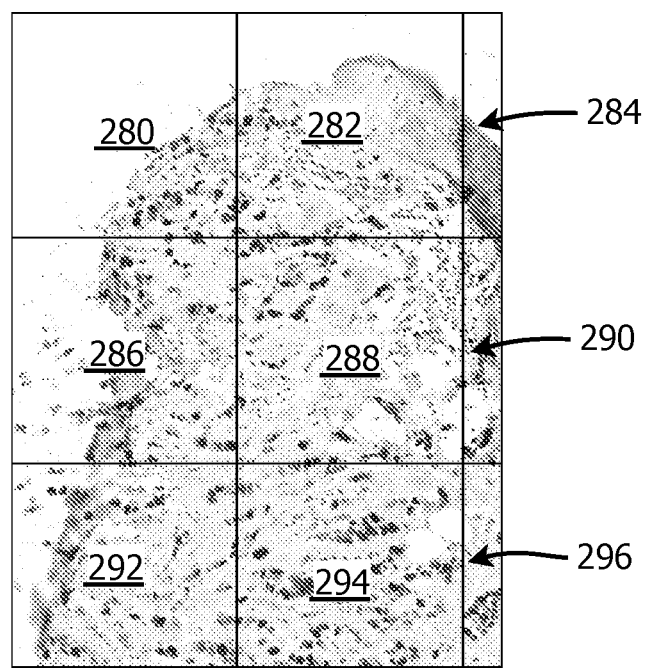
FIG. 4 is a representation of second level image regions of the pathology image shown in FIG. 2, in accordance with various embodiments.

In various embodiments, the pathology image data may include second level image files or records or representations thereof representing second level image regions 280-296 as shown in FIG. 4, wherein each of the second level image regions may represent more than one first level image region but with lower pixel density. In some embodiments, the second level image files representing the second level image regions 280-296 shown in FIG. 4 may each have ¼ pixel density (½ in the x dimension, and ½ in the y dimension) for the image regions as for the first level image files representing the pathology image 120 shown in FIG. 2.

For example, in some embodiments, the second level image file representing the second level image region 280 may have a pixel width and a pixel height of 512 and may include, first, second, third, and fourth portions or quadrants having pixel width and height of 256 pixels that represent the first level image regions 200, 202, 210, and 212 shown in FIG. 3 respectively. Similarly, the second level image file representing the second level image region 282 may have a pixel width and a pixel height of 512 and may include first, second, third, and fourth portions, each having a pixel width of 256 pixels and a pixel height of 256 pixels, representing the first level image regions 204, 206, 214, and 216 shown in FIG. 3 respectively.

Thus, in various embodiments, for each of the first level image regions 200-258 shown in FIG. 3, the pathology image data may include a first level image file acting as a first representation and a second level image file including a portion or quadrant acting as a second representation, the second representation having a smaller data size than the first representation. For example, in some embodiments, the second representation may have a smaller data size because it includes fewer pixels to represent the same region of the pathology image 120. In various embodiments, the second representation may have a pixel width smaller than a pixel width of the first representation and the second representation may have a pixel height smaller than a pixel height of the first representation. In various embodiments, this may facilitate use of the first and second representation at various zoom levels for pathological analysis.

In various embodiments, including the first and second representations of image regions may facilitate fast and efficient processing and/or manipulation of the pathology image 120 shown in FIG. 2 at various zoom levels or magnifications at least because it provides the flexibility of providing a small zoomed out version that is easily manipulated and/or processed (the second representation) or a larger zoomed in version that shows detail (the first representation). For example, in some embodiments, the system 10 may include the display 16 shown in FIG. 1 and a user may wish to view only a small region of the pathology image 120 shown in FIG. 2 in detail, such as, for example, only the first level image region 202 shown in FIG. 3, and so the image preparer 12 or another device in communication with the image source 14 may be configured to retrieve a first level image file representing the first level image region 202 and to produce signals representing the image file for causing the display 16 to display the first level image region 202.

In some embodiments, the user may wish to zoom out and view more context or generalities of the pathology image 120 as a whole, including more than one first level image region at once, such as for example, the second level image region 280 shown in FIG. 4 and so the image preparer 12 or another device in communication with the image source 14 may be configured to retrieve a second level image file representing the second level image region 280 and to produce signals representing the image file for causing the display to display the second level image region 280.

In various embodiments, because utility of analyzing or displaying the images may be limited by factors, such as, a user's vision capabilities, the resolution provided by the display 16, machine learning model properties, and/or other factors, it may be desirable to analyze or display a portion of the second level image file representing the second level image region 280 (acting as a second representation) instead of the first level image files representing the first level image regions 200, 202, 210, and 212 (acting as first representations). For example, it may be desirable to use a portion of the second level image file representing the second level image region 280 instead of any one of the first level image files representing the first level image regions 200, 202, 210, and 212 when both representations are generally indistinguishable for their purpose or close enough in content, because the sizes of the portions of the second level image file representing the first level image regions 200, 202, 210, and 212 may be smaller than the sizes of the first level image files representing the first level image regions 200, 202, 210, and 212. In some embodiments, such as where more than one of the first level image files representing the first level image regions included in a second level image region are generally indistinguishable from the respective portions of the second level image file representing the same image regions, it may be desirable to analyze or display the second level image file because it may require fewer computing resources to send a request and then a response for one, two, or three files, rather than for four separate files.

In some embodiments, a first representation of a first level image region may be indistinguishable from or close enough to a second representation of the same first level image region for various reasons. For example, the region may contain no tissue whatsoever, i.e., it may be essentially white (e.g., in brightfield imaging), or essentially black (e.g., in immunofluorescence imaging), for example. In some embodiments, a first representation of a first level image region may be indistinguishable from or close enough to a second representation of the same first level image region because the tissue may be out-of-focus in the image region, leading to loss of detail, though other parts of the image may still be in focus and/or useful for pathology. In various embodiments, this may happen commonly to slide images in pathology because gaining equal and ideal focus all over a slide may be a challenging problem. In some embodiments, a first representation may be indistinguishable from or close enough to a second representation because the first level image region may be a result of upscaling image content that had low resolution to begin with. In some embodiments, a first representation of a first level image region may be indistinguishable from or close enough to a second representation of the same first level image region for other reasons.

In some embodiments, a first representation of a first level image region may appear to be distinguishable from a second representation of the same first level image region to a layperson viewing the first and second representations, but the first representation may in fact be indistinguishable from or close enough to the second representation for the purposes of pathological analysis.

For example, in some embodiments, a first representation of a first level image region may be generally indistinguishable from a second representation of the same first level image region because the first representation may contain few or no relevant features for pathological analysis. This may be caused, for example, by there being an artefact in the image, such as, the tissue having been folded, which may hamper effective image analysis and further diagnosis based on the corresponding image region. This may be a common physical-world challenge for pathology imaging where tissue samples may be small and fragile and therefore not easy to handle. In some embodiments, a first representation of a first level image region may contain few or no relevant features for pathological analysis for other reasons.

In various embodiments, the image preparer 12 may be configured to determine whether the second representation can be used in place of the first representation and then, if so, to cause the second representation to be used in place of the first representation. In some embodiments, this may facilitate improved efficiency in manipulating and/or processing the image data.

In various embodiments, the image preparer 12 may be configured to, for each of the plurality of image regions, determine, based at least in part on the first representation of the image region, a first set of image properties and determine whether the first set of image properties meets first image property criteria. The image preparer 12 may be configured to, if the first set of image properties meets the first image property criteria, produce signals for causing the second representation to be used in place of the first representation.

In some embodiments, the first set of image properties may represent a difference between the first and second representations of the image region. For example, in some embodiments, the image preparer 12 may be configured to determine the difference between first and second representations of the first level image regions by comparing the first level image files with the second level image files. In various embodiments, if the difference between the first and second representations for a particular image region is small enough, then the image preparer 12 may be configured to cause the second representation to be used in place of the first representation. For example, in some embodiments, the image preparer 12 may be configured to generate updated pathology image data that does not include the first representation, but only includes the second representation for at least one image region.

Thus, in various embodiments, if the first and second representations are close enough in content, then the image preparer 12 may facilitate use of the second representations (having a smaller data size than the first representations) in place of the first representations. In various embodiments, this may facilitate faster and/or more efficient image manipulation and/or processing. In various embodiments, when used with pathology images, which can be very large and may include image areas where first and second representations are close in content, this may provide improvements in image processing performance, which may facilitate faster, more efficient and/or more accurate analysis of pathology images.

In various embodiments, whether the first set of image properties meets or does not meet the first image property criteria, the image preparer 12 may be configured to cause the second representation to be stored or kept such that the second representation is configured to be provided when requested. In various embodiments, the image preparer 12 may cause the second representation to be stored such that the second representation is configured to be provided when requested by including the second representation in the updated pathology image data, regardless of whether the first representation is kept or discarded. In various embodiments, keeping the second representation even when the first representation is also kept may facilitate functionality regarding image processing, manipulation, and/or analysis at various zoom levels or magnifications of the pathology image 120.

Image Preparer—Processor Circuit

Figure 5:
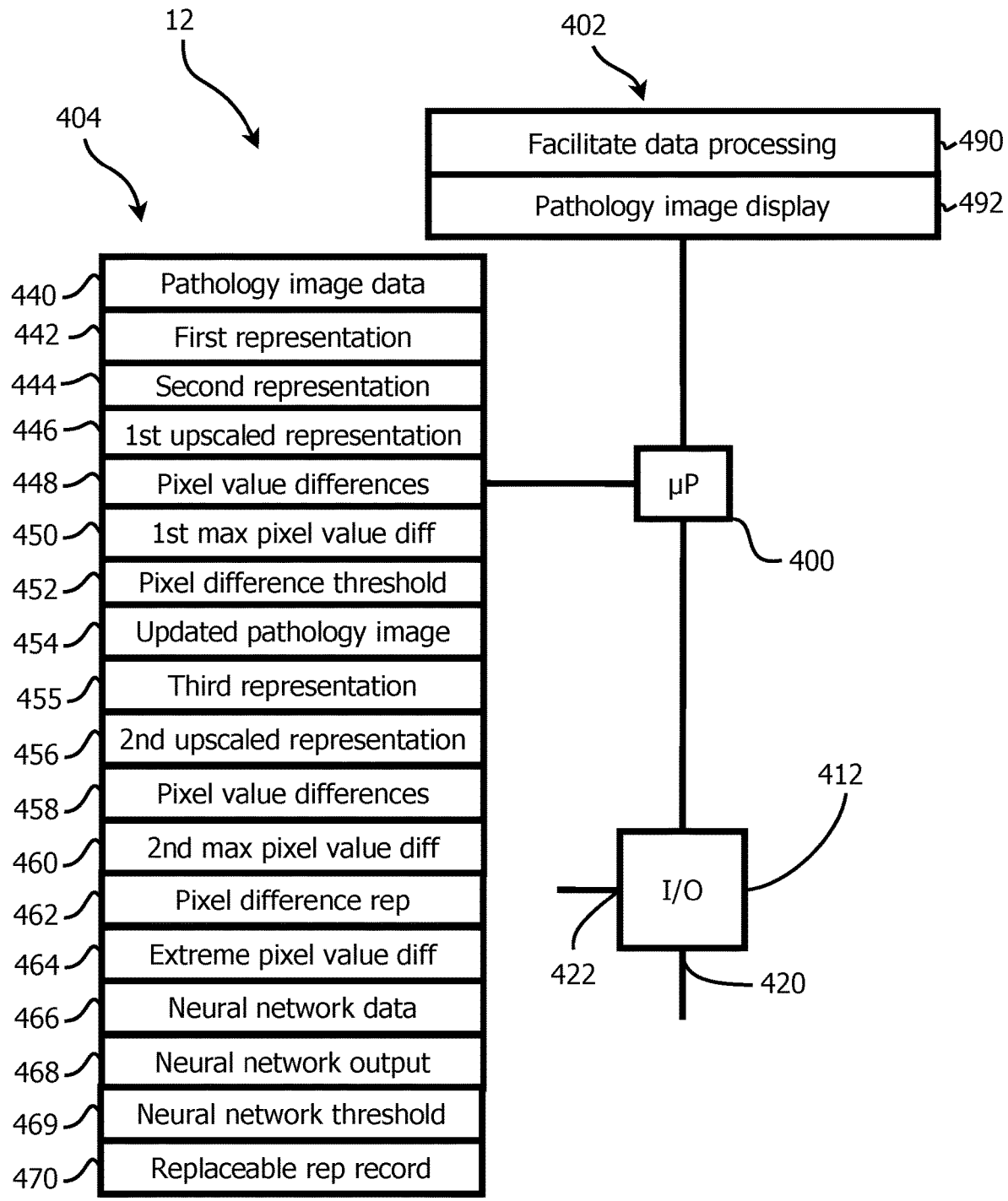
FIG. 5 is a schematic view of an image preparer of the system shown in FIG. 1, including a processor circuit, in accordance with various embodiments.

Referring now to FIG. 5, a schematic view of the image preparer 12 of the system shown in FIG. 1 according to various embodiments is shown. Referring to FIG. 5, the image preparer 12 includes a processor circuit including a preparer processor 400 and a program memory 402, a storage memory 404, and an input/output (I/O) interface 412, all of which are in communication with the preparer processor 400. In various embodiments, the preparer processor 400 may include one or more processing units, such as for example, a central processing unit (CPU), a graphics processing unit (GPU), and/or a field programmable gate array (FPGA). In some embodiments, any or all of the functionality of the image preparer 12 described herein may be implemented using one or more FPGAs.

The I/O interface 412 includes an interface 420 for communicating with the image source 14 shown in FIG. 1 and in some embodiments includes an interface 422 for communicating with the display 16 shown in FIG. 1. In some embodiments, the I/O interface 412 may include an interface for facilitating networked communication through a network such as the Internet and/or one or more interfaces for enabling user input via one or more user interface devices, such as, for example, a pointer and/or keyboard. In some embodiments, any or all of the interfaces may facilitate wireless and/or wired communication. In some embodiments, each of the interfaces may include one or more interfaces and/or some or all of the interfaces may be implemented as combined interfaces or a single interface.

In some embodiments, where a device is described herein as receiving or sending information, it may be understood that the device receives signals representing the information via an interface of the device or produces signals representing the information and transmits the signals to the other device via an interface of the device.

Processor-executable program codes for directing the preparer processor 400 to carry out various functions are stored in the program memory 402. Referring to FIG. 5, the program memory 402 includes a block of codes 490 for directing the image preparer 12 to perform facilitating processing of pathology images functions. In some embodiments, the program memory 402 may include a block of codes 492 for directing the image preparer 12 to perform facilitating pathology image displaying functions. In this specification, it may be stated that certain encoded entities such as applications or modules perform certain functions. Herein, when an application, module or encoded entity is described as taking an action, as part of, for example, a function or a method, it will be understood that at least one processor (e.g., the preparer processor 400) is directed to take the action by way of programmable codes or processor-executable codes or instructions defining or forming part of the application.

The storage memory 404 includes a plurality of storage locations including location 440 for storing pathology image data, location 442 for storing first representation data, location 444 for storing second representation data, location 446 for storing first upscaled representation data, location 448 for storing pixel value difference data, location 450 for storing first maximum pixel value difference data, location 452 for storing pixel difference threshold data, location 454 for storing updated pathology image data, location 455 for storing third representation data, location 456 for storing second upscaled representation data, location 458 for storing further pixel value difference data, location 460 for storing second maximum pixel value difference data, location 462 for storing pixel difference representation data, location 464 for storing extreme pixel value difference data, location 466 for storing neural network definition data, location 468 for storing neural network image property data, and location 469 for storing convolutional neural network output threshold data. In various embodiments, the plurality of storage locations may be stored in a database in the storage memory 404.

In various embodiments, the block of codes 490 and/or 492 may be integrated into a single block of codes or portions of the block of codes 490 and 492 may include one or more blocks of code stored in one or more separate locations in the program memory 402. In various embodiments, any or all of the locations 440-469 may be integrated and/or each may include one or more separate locations in the storage memory 404.

Each of the program memory 402 and storage memory 404 may be implemented as one or more storage devices including random access memory (RAM), a hard disk drive (HDD), a solid-state drive (SSD), a network drive, flash memory, a memory stick or card, any other form of non-transitory computer-readable memory or storage medium, and/or a combination thereof. In some embodiments, the program memory 402, the storage memory 404, and/or any portion thereof may be included in a device separate from the image preparer 12 and in communication with the image preparer 12 via the I/O interface 412, for example. In some embodiments, the functionality of the preparer processor 400 and/or the image preparer 12 as described herein may be implemented using a plurality of processors and/or a plurality of devices.

Preparer Operation

Figure 6:
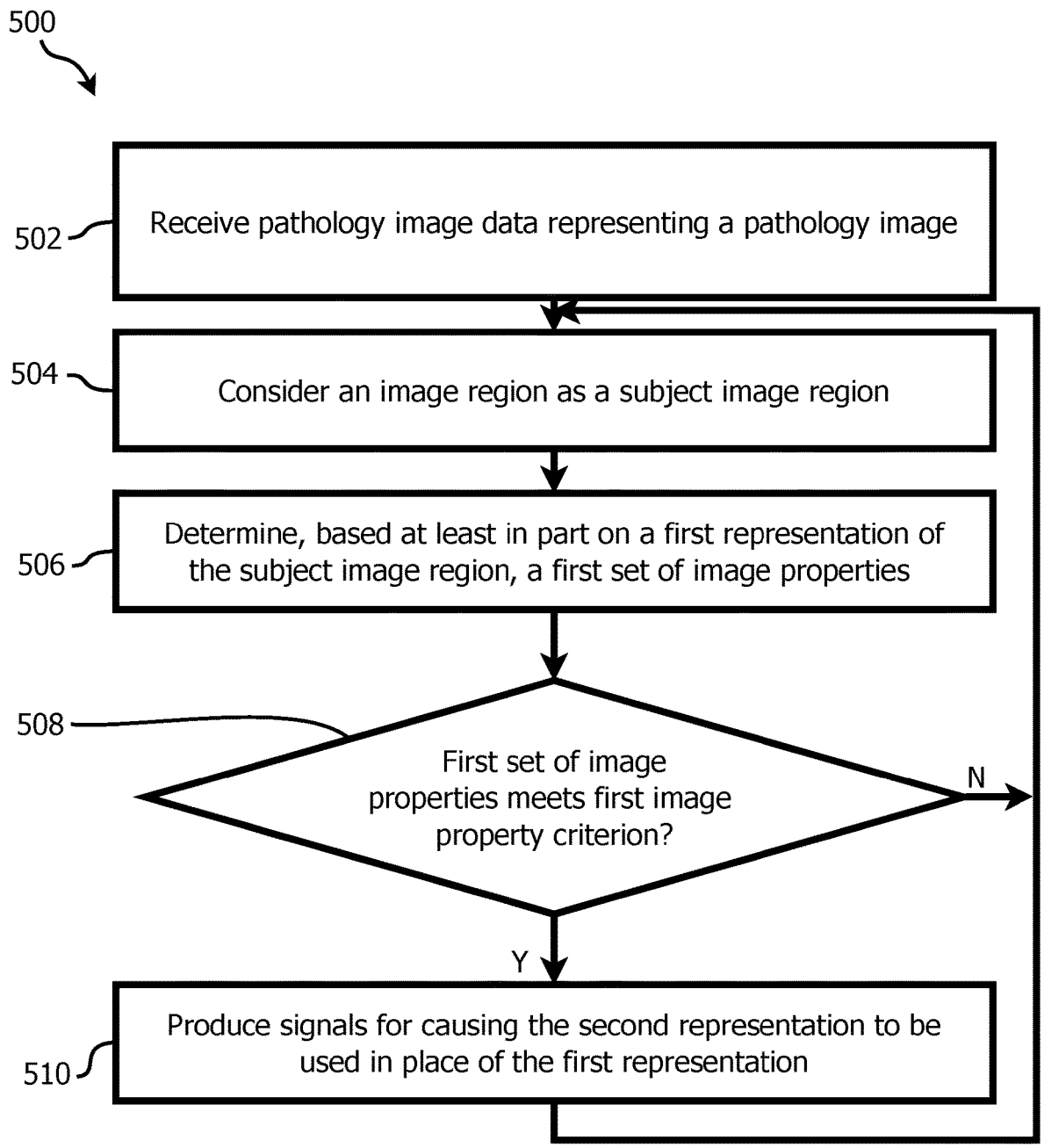
FIG. 6 is a flowchart depicting blocks of code for directing the image preparer shown in FIG. 5 to perform facilitating processing of pathology images functions, in accordance with various embodiments.

As discussed above, in various embodiments, the image preparer 12 shown in FIGS. 1 and 5 may be configured to facilitate processing of pathology images. Referring to FIG. 6, a flowchart depicting blocks of code for directing the preparer processor 400 shown in FIG. 5 to perform facilitating processing of pathology images in accordance with various embodiments is shown generally at 500. In various embodiments, the blocks of code included in the flowchart 500 may be encoded in the block of codes 490 of the program memory 402 shown in FIG. 5.

In some embodiments, the flowchart 500 may be executed to prepare or pre-process data for pathology images prior to the images being displayed and/or analyzed for pathology. For example, in some embodiments, the flowchart 500 may be executed to streamline or compress data representing pathology images that are stored initially as pyramid image representations. In various embodiments, the flowchart 500 may be embedded as a part of constructing the image pyramid representation, which may in some embodiments be preferable because the various image regions have already been loaded to memory. In various embodiments, as a result of execution of the flowchart 500 shown in FIG. 6, a representation of a pathology image may be stored more efficiently and effectively for image analysis in pathology. In various embodiments, because pathology images are commonly very large images which need to be analyzed both generally and at a high level detail, the preparing or pre-processing performed by the image preparer 12 may facilitate significant improvements in image processing efficiency and/or speed.

Referring to FIG. 6, the flowchart 500 begins with block 502 which directs the preparer processor 400 to receive pathology image data representing a pathology image having a plurality of image regions, wherein the pathology image data includes, for each of the plurality of image regions, a respective plurality of representations of the image region including a first representation and a second representation, the second representation having a smaller data size than the first representation.

In some embodiments, block 502 of the flowchart 500 shown in FIG. 6 may direct the preparer processor 400 shown in FIG. 5 to receive pathology image data representing the pathology image 120 shown in FIG. 2 including respective first level image files representing each of the first level image regions 200-258 shown in FIG. 3 and respective second level image files representing each of the second level image regions 280-296 shown in FIG. 4 from the image source 14 shown in FIG. 1. In various embodiments, the first and second level image files may have been previously derived from the pathology image 120 shown in FIG. 2. In various embodiments, the first and second level image files may not have been derived previously, but instead block 502 may include code directing the preparer processor 400 to derive the first and second level image files from the pathology image 120 shown in FIG. 2. For example, in various embodiments, a block of codes may direct the preparer processor 400 to first divide the pathology image 120 into the first level image files as generally shown in FIG. 3. In some embodiments, the block may direct the preparer processor 400 to generate the second level image files by joining four first level image files together, and then downscaling the result. For example, an intermediate image representing the first level image regions 200, 202, 210, and 212 at the same pixel density may be generated. In various embodiments this intermediate image may then be downscaled, for example using Lanczos resampling, to obtain the second level image file representing the second level image region 280, which has a lower pixel density than any of the first level image regions 200, 202, 210, and 212.

Block 502 may direct the preparer processor 400 to store the first and second level image files representing the first and second level image regions 200-258 and 280-296 shown in FIGS. 3 and 4 in the location 440 of the storage memory 404.

In various embodiments, the image files may be stored in a format that allows for rasterization, such as, for example, JPEG, PNG, OpenEXR, or another raster format, or another image file format, such as a vector format. In various embodiments, such as in brightfield microscopy, the image files may be 8-bit lossy-compressed JPEGs. In various embodiments, such as in immunofluorescence microscopy, the image files may be 16-bit lossless-compressed PNGs. In various embodiments, alternative and/or additional levels of image files representing additional levels of image regions may be included in the pathology image data.

Referring to FIG. 6, the flowchart 500 continues at block 504, which directs the preparer processor 400 to consider an image region of the image 120 as a subject image region. In various embodiments, block 504 may eventually be executed for each of the first level image regions 200-258 show in FIG. 3. For example, in a first execution of block 504, block 504 may direct the preparer processor 400 to consider the first level image region 200 shown in FIG. 3 as the subject image region.

In some embodiments, block 504 may direct the preparer processor 400 to identify the first level image file representing the first level image region 200 from the pathology image data stored in the location 440 of the storage memory 404 and to store a representation of the first level image file in the location 442 as a first representation of the subject image region. In some embodiments, block 504 may direct the preparer processor 400 to identify, from the pathology image data stored in the location 440 of the storage memory 404, the second level image file representing the second level image region 280 that includes the first level image region 200 and to store in the location 444, a representation of or a view to the portion of the second level image file that represents the same region as the first level image file stored in the location 442. In various embodiments the portion of the second level image file stored in the location 444 of the storage memory 404 that represents the same region as the first level image file stored in the location 442 may act as the second representation.

Accordingly, in various embodiments, first and second representations of the first level image region 200 shown in FIG. 3 may be identified and stored in the locations 442 and 444 of the storage memory 404, wherein the second representation has a smaller data size than the first representation. The second representation may have a smaller data size because it has a lower pixel density and/or a smaller pixel width and height, to represent the same image region, for example. In various embodiments, the second representation may have half the pixel width and half the pixel height compared to the first representation for the same image region, for example.

Block 506 then directs the preparer processor 400 to determine, based at least in part on the first representation of the subject image region, a first set of image properties. In some embodiments, the first set of image properties may be indicative of whether the second representation of the subject image region can be used in place of the first representation, the second representation having a smaller data size than the first representation. For example, in some embodiments, the first set of image properties may represent a difference between first and second representations of the image region.

In some embodiments, block 506 may direct the preparer processor 400 to determine based on at least the first and second representations, a first image difference representing the difference between the first and second representations of the image region. In various embodiments, using the first image difference representing the difference between the first and second representations may facilitate ease of analysis in determining whether the first representation is replaceable by the second representation.

Figure 7:
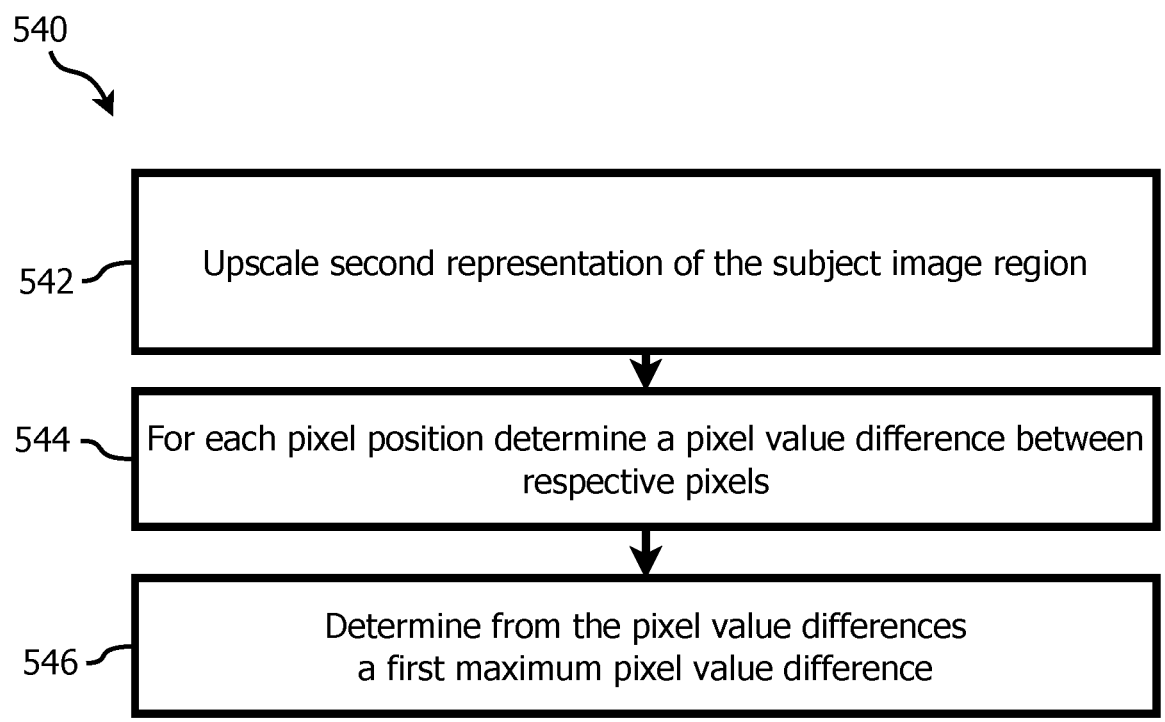
FIG. 7 is a flowchart depicting blocks of code that may be included in the flowchart shown in FIG. 6, in accordance with various embodiments.

Referring to FIG. 7, there is shown a flowchart 540 depicting blocks of code that may be included in the block 506 in accordance with various embodiments. The flowchart 540 begins with block 542, which directs the preparer processor 400 to upscale the second representation of the subject image region to generate a first upscaled representation of the image region, the first upscaled representation of the image region having the same pixel dimensions as the first representation of the image region. In some embodiments, block 542 may direct the preparer processor 400 to read the second representation from the location 444 of the storage memory 404 and to store the first upscaled representation in the location 446 of the storage memory 404. In some embodiments, a quadrant or portion of the second level image file may act as the second representation, for example. In some embodiments, the first upscaled representation may be stored as an image file. In some embodiments, the upscaling may be done using bilinear or bicubic interpolation, for example.

Referring to FIG. 7, block 544 then directs the preparer processor 400 to, for each pixel position in the first representation and the first upscaled representation, determine a pixel value difference between respective pixels of the first representation and the first upscaled representation. For example, in some embodiments, block 544 may direct the preparer processor 400 to compare the pixel value in each pixel position in the first representation stored in the location 442 of FIG. 5 with a pixel value in a corresponding pixel position in the first upscaled representation stored in the location 446 and to determine a pixel value difference. In various embodiments, block 544 may direct the preparer processor 400 to store the determined pixel value differences in the location 448 of the storage memory 404 shown in FIG. 5, for example, as an array. In various embodiments, upscaling and then determining the pixel value differences may facilitate simple and/or efficient identification of portions of the first representation that are not well represented by the second representation.

Block 546 then directs the preparer processor 400 to determine from the pixel value differences, a first maximum pixel value difference. In various embodiments, block 546 may direct the preparer processor 400 to read the pixel value differences stored in the location 448 and to store the largest absolute value of these as the first maximum pixel value difference in the location 450 of the storage memory 404.

In various embodiments, the first maximum pixel value difference stored in the location 450 of the storage memory 404 and/or the pixel value differences stored in the location 448 of the storage memory 404 may act as the first set of image properties determined at block 506 of the flowchart 500 shown in FIG. 6.

Referring to FIG. 6, block 508 directs the preparer processor 400 to determine whether the first set of image properties meets first image property criteria. In various embodiments, block 508 may direct the preparer processor 400 to compare the first maximum pixel value difference stored in the location 450 of the storage memory 404 shown in FIG. 5 with a first maximum pixel difference threshold stored in the location 452 of the storage memory 404. In some embodiments, the first maximum pixel difference threshold stored in the location 452 may be a value that has been previously determined. In various embodiments, the first maximum pixel difference threshold stored in the location 452 may be a user-configurable parameter that may be adjusted depending on the application. In various embodiments, it may be possible to find threshold values that work across wide ranges of applications. In some embodiments, such as, in the case of 8-bit image data, for example, where decimal pixel intensities vary in the range between 0 and 255, a suitable pixel difference threshold for the first maximum pixel value difference may be about 20, for example.

In various embodiments, identifying the maximum pixel value difference and using it as representative of the first image difference may facilitate simple and/or efficient application of criteria for avoiding use of the second representation in place of the first representation when the second representation does not include pathologically relevant features included in the first representation.

Referring to FIG. 6, in various embodiments, if at block 508, the preparer processor 400 determines that the first set of image properties meets the first image property criteria, the preparer processor 400 may be directed to proceed to block 510. For example, in some embodiments, if the first maximum pixel value difference stored in the location 450 is less than the first maximum pixel difference threshold stored in the location 452, the preparer processor 400 may be directed to proceed to block 510.

Block 510 directs the preparer processor 400 to produce signals for causing the second representation to be used in place of the first representation. In some embodiments, block 510 may direct the preparer processor 400 to update the pathology image data to remove the first representation. For example, in some embodiments, block 510 may direct the preparer processor 400 to delete the first level image file representing the first level image region 200 from the pathology image data stored in the location 440 of the storage memory 404. In various embodiments, removing the first level image file representing the first level image region 200 shown in FIG. 3 from the pathology image data may facilitate use of the corresponding quadrant of the second level image file representing the second level image region 280 shown in FIG. 4 in its place. In some embodiments, block 510 may direct the preparer processor 400 to produce signals representing updated pathology image data and store the updated pathology image data in the location 454 of the storage memory 404, the updated pathology image data not including the first level image file representing the first level image region 200.

Referring to FIG. 6, after block 510 has been executed, the preparer processor 400 may be directed to return to block 504 and a new image region may be considered the subject image region. Alternatively, if at block 508 the preparer processor 400 determines that the first set of image properties does not meet the first image property criteria, the preparer processor 400 may be directed to keep both the first and second representations of the subject image region in the updated pathology image data stored at location 454 of the storage memory 404 and the preparer processor 400 may return to block 504 and a new image region may be considered to be the subject image region.

In various embodiments, blocks 504, 506, 508, and in some cases block 510 may then be executed with respect to the newly considered subject image region. In various embodiments, blocks 504-508 and in some cases 510 may be executed for each of the first level image regions 200-258 shown in FIG. 3. In various embodiments, once all of the first level image regions 200-258 shown in FIG. 3 have been considered, the flowchart 500 may end. In various embodiments, once the flowchart 500 has been executed, the updated pathology image data stored in the location 454 may be a streamlined or more efficient representation of the pathology image 120 shown in FIG. 2.

In various embodiments, after the flowchart 500 has been completed, the preparer processor 400 may be directed to produce signals representing the updated pathology image data for causing the updated pathology image data to be sent to the image source 14. In various embodiments, the image source 14 may be configured to replace the pathology image data associated with the pathology image 120 with the updated pathology image data.

In some embodiments, the flowchart 500 may be executed for a plurality of pathology images generally similar to the pathology image 120 shown in FIG. 2, such that updated pathology image data representing each of the pathology images is generated and sent to the image source 14 for later processing and/or display. In some embodiments, the pathology images may include individual images that belong to a "Z-stack" of pathology images taken of the generally same subject, but at different focus distances. In some embodiments, the pathology images may include individual images that may be taken of the generally same subject, but at different times, therefore comprising a time series. In various embodiments, the pathology images may include individual images that may represent different biopsies (samples) taken from different locations of the same patient or other subject. In some embodiments, the pathology images may include individual images that may represent different sections of the same physical sample taken from a patient. In various embodiments, the pathology images may include individual images that may represent samples collected from different individual animals, in order to perform a drug efficacy experiment, for example. In some embodiments, the pathology images may include individual images that may not be directly related to each other in any particular way.

In various embodiments, whether the first set of image properties meets or does not meet the first image property criteria, the second representation may be included in the updated pathology image data such that the second representation is configured to be provided when requested. In various embodiments, this may facilitate processing and/or displaying of the second representation when the detail provided by the first representation is not necessary and/or is redundant in view of the information provided by the second representation. In various embodiments, this may facilitate efficient and/or fast processing and/or display of various zoom levels of the pathology image 120 shown in FIG. 2, which may be particularly advantageous for pathology images where both high detail and a general understanding/view of the image may be required and/or desirable.

In various embodiments, updating the pathology image data to not include the first level image file representing the first level image region 200 may cause the second representation to be later used or displayed in place of the first representation. For example, in some embodiments, after the flowchart 500 has been completed for the pathology image 120, the image preparer 12 or another device in communication with the image source 14 may receive a request for a first representation, for which the second representation is to be used in place of. For example, in some embodiments, the request may come from the display 16 or another device configured to analyze the pathology image 120.

In various embodiments, the image preparer 12 or the other device in communication with the image source 14 may be configured to produce signals for causing the second representation to be provided in place of the first representation in response to the request for the first representation. In embodiments where the image preparer 12 is so configured, the image preparer 12 may act as an image providing device. In some embodiments, another device separate from the image preparer 12, such as, for example, the display 16 or another device in communication with the display 16 may act as the image providing device.

Figure 8:
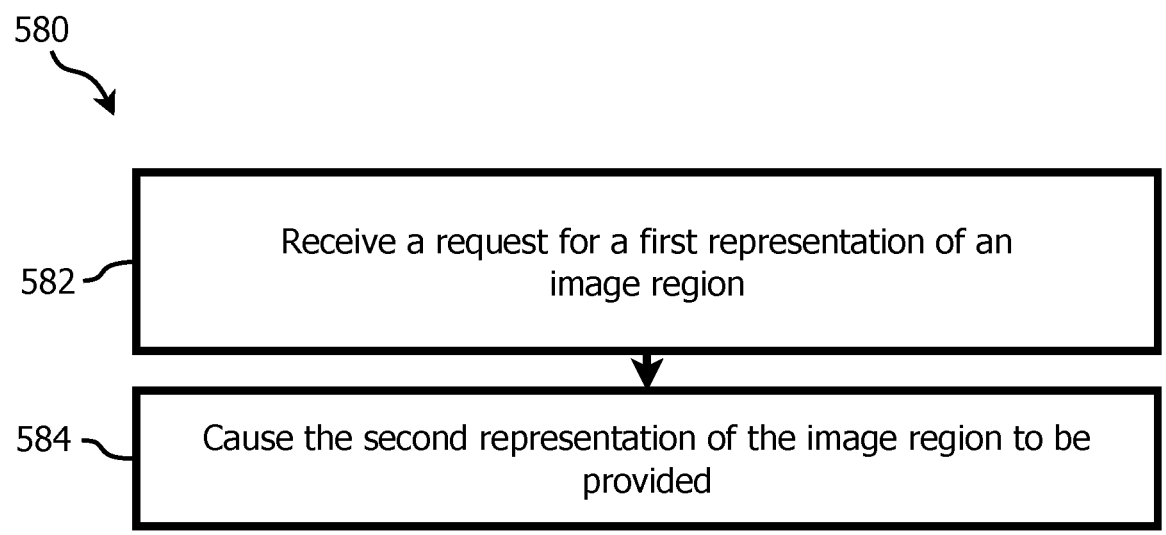
FIG. 8 is a flowchart depicting blocks of code for directing the image preparer shown in FIG. 5 to perform displaying pathology images functions, in accordance with various embodiments.

Referring to FIG. 8, a flowchart depicting blocks of code for directing the preparer processor 400 shown in FIG. 5 to perform displaying pathology images functions in accordance with various embodiments is shown generally at 580. The blocks of code included in the flowchart 580 may be encoded in the block of codes 492 of the program memory 402 shown in FIG. 5, for example.

Referring to FIG. 8, the flowchart begins with block 582, which directs the preparer processor 400 to receive a request for a first representation of an image region. In some embodiments, for example, a pathologist or user may wish to view the first level image region 200 shown in FIG. 3 in detail and so the user may cause a request for the first representation of the first level image region 200 to be sent to the image preparer 12. For example, in some embodiments, the request may be generated using a user interface including a pointer and/or the display 16, for example, in communication with the image preparer 12.

In some embodiments, block 582 may direct the preparer processor 400 to determine whether a second representation should be provided in place of the first representation. In some embodiments, block 582 may direct the preparer processor 400 to determine whether a second representation should be provided in place of the first representation by determining whether the first representation is included in the updated pathology image data stored in the location 454. In some embodiments, block 582 may direct the preparer processor 400 to read the updated pathology data stored in the location 454 of the storage memory 404 to look for the first level image file representing the first level image region 200.

In various embodiments, if the first level image file representing the first level image region cannot be found in the updated pathology data, it may be determined that a second representation should be provided in place of the first representation and block 582 may direct the preparer processor 400 to proceed to block 584.

In some embodiments, if at block 582 it is determined that the second representation should not be provided in place of the first representation, block 582 may direct the preparer processor 400 to cause the first representation to be provided. For example, if the first level image file representing the first level image region could be found in the updated pathology data, block 582 may direct the preparer processor 400 to proceed to cause the first level image file to be provided.

Block 584 directs the preparer processor 400 to cause a second representation of the image region to be provided. In some embodiments, block 584 may direct the preparer processor 400 to produce signals for causing the second representation of the image region to be displayed by the display 16. In various embodiments, block 584 may direct the preparer processor 400 to find the second level image file including a portion representing the first level image region 200. Block 584 may direct the preparer processor 400 to produce signals representing the portion of the second level image file representing the first level image region 200 for causing a representation of the portion of the second level image file to be sent to the display 16 via the interface 422.

Figure 9:
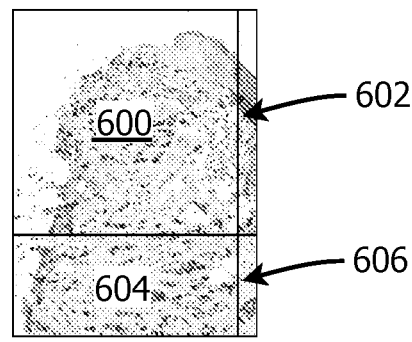
FIG. 9 is a representation of third level image regions of the pathology image shown in FIG. 2, in accordance with various embodiments.

In some embodiments, the pathology data may include additional or alternative image files representing additional or alternative image levels. For example, in some embodiments, block 502 of the flowchart 500 shown in FIG. 6 may direct the preparer processor 400 to receive and store third level image files representing third level image regions 600, 602, 604, and 606 as shown in FIG. 9. In various embodiments, the third level image files representing the third level image regions 600, 602, 604, and 606 may have lower pixel density than the second level image files representing the second level image regions 280-296 shown in FIG. 4. For example, in some embodiments, the third level image file representing the third level image region 600 shown in FIG. 9 may have a pixel width of 512 pixels and a pixel height of 512 pixels for representing an area that is the same as the total area of the second level image regions 280, 282, 286, and 288 shown in FIG. 4. In various embodiments, the third level image files may be stored in the location 455 of the storage memory 404.

In some embodiments, respective portions of the third level image files may represent first or second level image regions, but using fewer pixels than are used to represent such regions by the first and second level image files. In various embodiments, each of the respective portions of the third level image files representing the first level image regions may act as third representations of the first level image regions, the third representations having a smaller data size than the first and the second representations discussed above. In various embodiments, each of the respective portions of the third level image files representing the second level image regions may act as third representations of the second level image regions, the third representations having a smaller data size than the second representations discussed above.

Referring to FIG. 6, in some embodiments, if at block 508, it is determined that the first representation is replaceable by the second representation, block 508 may direct the preparer processor 400 to determine whether the second representation is also replaceable by the third representation. In various embodiments, such a second level replacement may facilitate further efficiency, speed, and/or cost improvements. In various embodiments, block 508 may direct the preparer processor 400 to determine, based at least in part on the second representation of the subject image region, a second set of image properties, determine whether the second set of image properties meets second image property criteria, and, if the second set of image properties meets the second image property criteria, produce signals for causing the third representation to be used in place of the first representation. In some embodiments, the above steps may only be performed if it is first determined that the first representation is replaceable by the second representation.

In some embodiments, a determination that the second set of image properties meets the second image property criteria may result in determining that the first set of image properties does not meet the first image property criteria and thus the second representation may not be used in place of the first representation because a better candidate (i.e., the third representation) should be used. Thus, in various embodiments, determining whether the first set of image properties meets the first image property criteria may involve determining whether the second set of image properties meets the second image property criteria.

Figure 10:
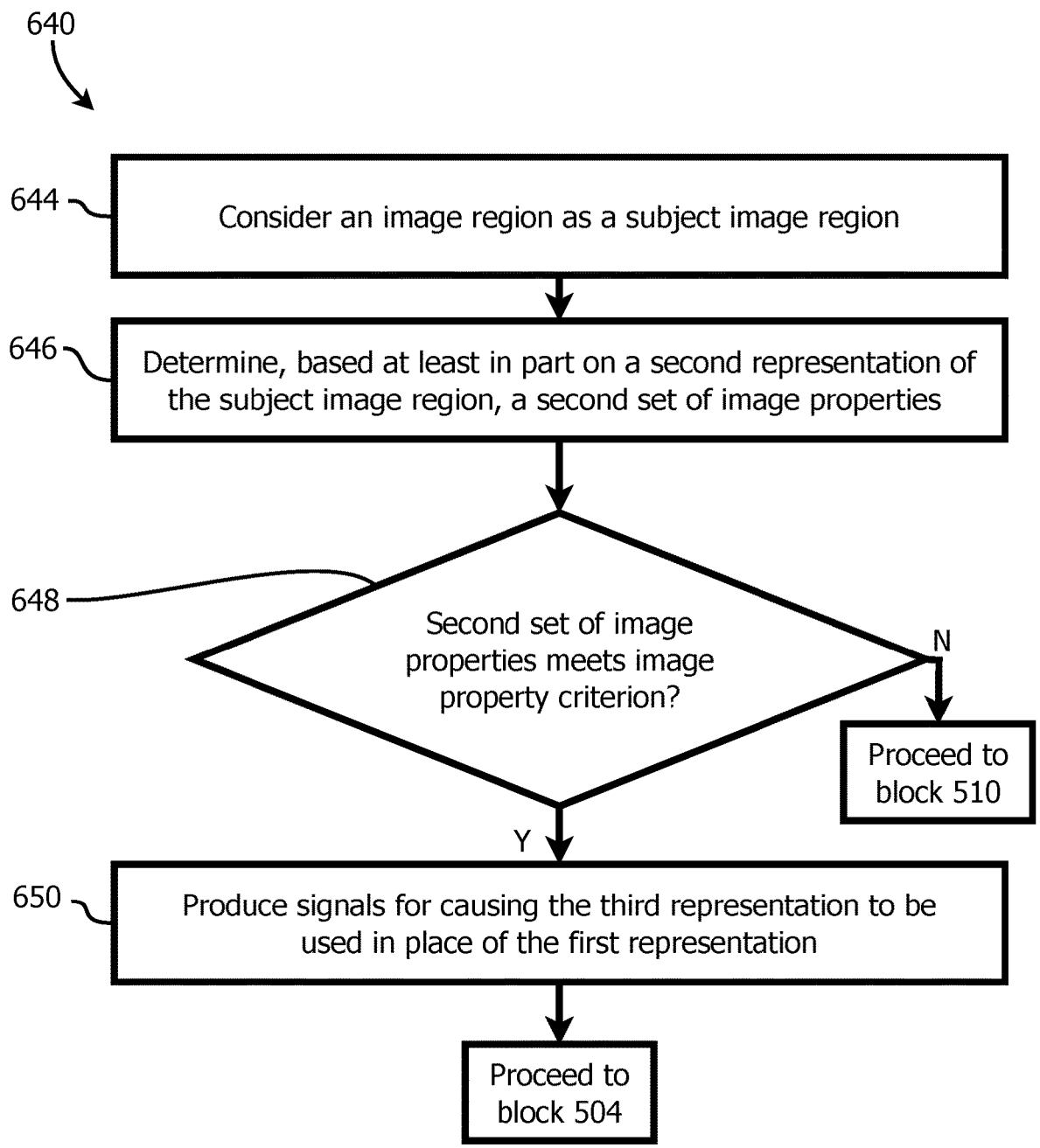
FIG. 10 is a flowchart depicting blocks of code that may be included in the flowchart shown in FIG. 6, in accordance with various embodiments.

In some embodiments, block 508 may direct the preparer processor 400 to proceed generally as described above regarding the first representation and the second representation, but this time with the second representation and the third representation to determine whether the third representation could be used in place of the second representation and thus in place of the first representation if it was previously or concurrently determined that the second representation can be used in place of the first representation. Referring now to FIG. 10, there is shown a flowchart 640 representing blocks of code that may be included in the block 510 according to various embodiments.

The flowchart 640 begins with block 644, which directs the preparer processor 400 to consider an image region as a subject image region. In some embodiments, block 644 may direct the preparer processor 400 to consider a second level image region as the subject image region. In some embodiments, block 644 may direct the preparer processor 400 to consider as the subject second level image region, the second level image region that contains the subject first level image region considered at block 504 of the flowchart 500 in FIG. 6. In some embodiments, block 644 may direct the preparer processor 400 to only proceed with execution of the flowchart 640 for a second level image region for which all of the first representations contained therein have been previously determined to be unnecessary, such that the entirety of the second level image file representing the second level image region has been found as useable in place of the respective first level image files representing the second level image region. Accordingly, in various embodiments block 644 may direct the preparer processor 400 to determine whether the subject second level image region includes first level image regions for which all of the first representations have been found replaceable by the respective second representations. If it is determined that not all first level image regions within the subject second level image region have been found replaceable then the flowchart 640 may end and the preparer processor 400 may be directed to proceed to block 510 of the flowchart 500 shown in FIG. 6. In various embodiments, this may facilitate implementation simplicity to avoid a need to use a first level image file in place of a portion of a second level image file, when the second level image file may be requested (based on a zoom level a user may be viewing) but the corresponding second level image file has been removed or discarded.

In some embodiments, block 644 may direct the preparer processor 400 to identify the second level image file representing the second level image region 280 from the pathology image data stored in the location 440 of the storage memory 404 and to store a representation of the second level image file in the location 444 as a second representation of the subject image region. In some embodiments, block 644 may direct the preparer processor 400 to identify, from the pathology image data stored in the location 440 of the storage memory 404, the third level image file representing the third level image region 600 shown in FIG. 8 that includes the second level image region 280 and to store in the location 455, a representation of or a view to a portion of the third level image file that represents the same region as the second level image file stored in the location 444.

Accordingly, in various embodiments, second and third representations of the second level image region 280 shown in FIG. 4 may be identified and/or stored in the locations 444 and 455 of the storage memory 404, wherein the third representation has a smaller data size than the second representation.

Referring still to FIG. 10, block 646 may then direct the preparer processor 400 to determine, based at least in part on the second representation of the image region, a second set of image properties. In various embodiments, block 646 of the flowchart 640 shown in FIG. 10 may function generally similarly to block 506 shown in FIG. 6 and described above.

Block 646 may direct the preparer processor 400 to upscale the third representation of the subject image region from the location 455 of the storage memory 404 to generate a second upscaled representation of the image region, the second upscaled representation of the image region having the same pixel dimensions as the second representation of the subject image region. In various embodiments, block 646 may include a block of code functionally generally as described above having regard to block 542 of the flowchart 540 shown in FIG. 7 but using the second representations and portions or quadrants of the third representations instead of the first representations and portions or quadrants of the second representations. In various embodiments, block 646 may direct the preparer processor 400 to store the second upscaled representation in the location 456 of the storage memory 404.

Block 646 may direct the preparer processor 400 to, for each pixel position in the second representation and the second upscaled representation, determine a pixel value difference between respective pixels of the second representation and the second upscaled representation, functionally generally as described above having regard to block 544 of the flowchart 540 shown in FIG. 7. Block 646 may direct the preparer processor 400 to store the determined pixel value differences in the location 458 of the storage memory 404.

Block 646 may direct the preparer processor 400 to determine from the pixel value differences, a second maximum pixel value difference. In various embodiments, block 646 may include code functionally generally similar to block 546 of the flowchart 540 shown in FIG. 7. In some embodiments, block 646 may direct the preparer processor 400 to read the pixel value differences stored in the location 458 and to store the largest of these as the second maximum pixel value difference in the location 460 of the storage memory 404.

In various embodiments, the second maximum pixel value difference stored in the location 460 of the storage memory 404 and/or the pixel value differences stored in the location 458 of the storage memory 404 may act as the second set of image properties determined at block 646 of the flowchart 640 shown in FIG. 10.

Referring to FIG. 10, in various embodiments, block 648 may then direct the preparer processor 400 to determine whether the second set of image properties meets second image property criteria. In some embodiments, block 648 may direct the preparer processor 400 to compare the second maximum pixel value difference stored in the location 460 of the storage memory 404 with a second maximum pixel difference threshold stored in the storage memory 404 (e.g., in the location 452 of the storage memory 404). In some embodiments, the second maximum pixel difference threshold may be the same as the first maximum pixel difference threshold described above.

In various embodiments, the second maximum pixel difference threshold may have a lower magnitude than the first maximum pixel difference threshold described above. Accordingly, in some embodiments, certain image content may lead to discarding the corresponding image file if it is a first representation, but keeping similar image content if found in a second representation. This may be desirable, because for a given region of the pathology image 120, the first representations generally require the most storage capacity in total. Accordingly, in various embodiments, the greatest benefits from discarding image content may generally come from discarding the first representations. Further, any second representation may generally cover a larger area of the pathology image 120 than does any first representation having a similar data size. Thus, when moving from considering the first representations to evaluating the corresponding second representations, the potential benefits from discarding data may generally decrease, whereas the possible adverse effects of doing so may increase. Therefore, in various embodiments, it may be desirable to discard a second representation relatively less aggressively than a corresponding first representation.

In various embodiments, if the first maximum pixel difference threshold for the first level decision was 20, the second maximum pixel difference threshold may be $20/2^2=5$, for example. In various embodiments where subsequent levels are used, subsequent thresholds may be $20/4^2=1.25$, for example (and then $20/8^2$, $20/16^2$, and so on). In various embodiments, this may facilitate the threshold value dropping rapidly, when considering subsequent representations.

In various embodiments, if at block 648 of the flowchart 640 shown in FIG. 10, the preparer processor 400 determines that the second set of image properties meets the second image criteria, the preparer processor 400 may be directed to proceed to block 650 which directs the preparer processor 400 to produce signals for causing the third representation to be used in place of the first representation. In some embodiments, block 650 may thus direct the preparer processor 400 to produce signals for causing the third representation to be used in place of the second representation, and consequently in place of the first representation.

In some embodiments, block 650 may direct the preparer processor 400 to update the pathology image data to remove the second representation and the first representation(s) of the subject image region. For example, in some embodiments, block 650 may direct the preparer processor 400 to delete the first and second level image files representing the second level image region 280 from the pathology image data stored in the location 440 of the storage memory 404.

In various embodiments, removing the first and second level image files representing the second level image region 280 shown in FIG. 4 from the pathology image data may facilitate use of a portion of the third level image file representing the second level image region 280 in place of the first representations. In some embodiments, block 650 may direct the preparer processor 400 to produce signals representing updated pathology image data and store the updated pathology image data in the location 454 of the storage memory 404, the updated pathology image data not including the first or second level image files representing the second level image region 280.

In various embodiments after block 650 has been executed, the preparer processor 400 may be directed to return to block 504 of the flowchart 500 shown in FIG. 6 and to consider a next first level image region as the subject first level image region.

In various embodiments, if at block 648 it is determined that the second set of image properties does not meet the second image property criteria, the preparer processor 400 may be directed to proceed to block 510 of the flowchart 500 shown in FIG. 6, such that signals are produced for causing the second representation to be used in place of the first representation, generally as described above.

Various Embodiments

In some embodiments, the image preparer 12 may be configured to execute blocks of code generally similar to the blocks of code included in the flowchart 500 shown in FIG. 6 but with blocks 506 and 508 including additional or alternative blocks of code for applying additional or alternative criteria to those described above. For example, in some embodiments, block 506 may include code that directs the preparer processor 400 to identify from the absolute pixel value differences stored in the location 448, upper absolute pixel value differences, which are in an upper percentile of the absolute pixel value differences. For example, in some embodiments, block 506 may direct the preparer processor 400 to identify upper absolute pixel value differences, which are in the top 99.9th percentile of the absolute pixel value differences.

In some embodiments, block 506 may direct the preparer processor 400 to store the lowest pixel value difference that is in the top 99.9th percentile of the pixel value differences in the location 462 of the storage memory 404. In various embodiments, this value may be treated as the first maximum pixel value difference. In various embodiments, block 508 may direct the preparer processor 400 to determine whether the pixel value difference stored in the location 462 of the storage memory 404 is less than a percentile pixel difference threshold to determine whether the first set of image properties meets the first image property criteria. In various embodiments, this may facilitate ignoring individual outlier pixels. In various embodiments, ignoring individual outlier pixels may be advantageous because it may let the image preparer 12 obtain further processing and storage benefits.

In various embodiments, instead of or in addition to storing the largest absolute value as the first maximum pixel value difference, block 506 may direct the preparer processor 400 to identify the largest (non-absolute) pixel value difference (i.e., largest magnitude positive number), and separately the lowest (non-absolute) pixel value difference (i.e., largest magnitude negative number) (or only one of these). In some embodiments, doing so may cause the bright-side differences to be treated differently from the dark-side differences. Each extreme value may represent a separate image property. In various embodiments, each image property may be compared to corresponding image property criteria. In various embodiments, percentile-based values may be used to represent the largest and the lowest (non-absolute) pixel value differences.

Figure 11:
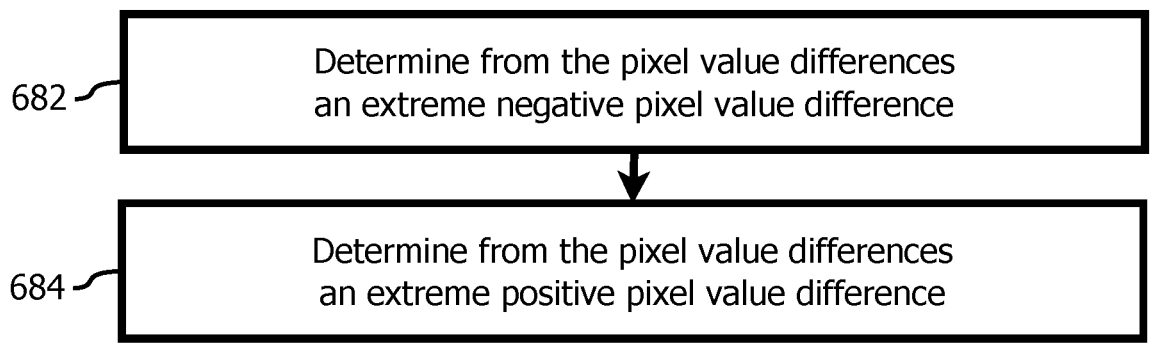
FIG. 11 is a flowchart depicting blocks of code that may be included in the flowchart shown in FIG. 6, in accordance with various embodiments.

Referring to FIG. 11, there is shown blocks of code 682 and 684 that may be included in place of or in addition to block 546 of the flowchart 540 in accordance with various embodiments. Referring to FIG. 11, block 682 directs the preparer processor 400 to determine from the pixel value differences, an extreme negative pixel value difference. In various embodiments, a negative pixel value difference may arise when the first representation has a darker pixel than the first upscaled representation. For example, in some embodiments, block 682 may direct the preparer processor 400 to identify the lowest pixel value difference from the pixel value differences stored in the location 448 of the storage memory 404 shown in FIG. 5, as the extreme negative pixel value difference. In some embodiments, the extreme negative pixel value difference may have the largest absolute value or magnitude of all negative pixel value differences included in the pixel value differences stored in the location 448. Block 682 may direct the preparer processor 400 to store the extreme negative pixel value difference in the location 464 of the storage memory 404, for example.

Referring to FIG. 11, block 682 directs the preparer processor 400 to determine from the pixel value differences, an extreme positive pixel value difference. For example, in some embodiments, block 682 may direct the preparer processor 400 to identify the highest pixel value difference from the pixel value differences stored in the location 448 of the storage memory 404 shown in FIG. 5, as the extreme positive pixel value difference. In some embodiments, the extreme positive pixel value difference may have the largest absolute value or magnitude of all positive pixel value differences included in the pixel value differences stored in the location 448. Block 684 may direct the preparer processor 400 to store the extreme positive pixel value difference in the location 464 of the storage memory 404, for example.

In various embodiments, block 508 of the flowchart 500 shown in FIG. 7 may include code for directing the preparer processor 400 to compare the extreme negative pixel value difference with an extreme negative pixel difference threshold and to compare the extreme positive pixel value difference with an extreme positive pixel difference threshold, the extreme positive pixel difference threshold being different in magnitude from the extreme negative pixel difference threshold. For example, for some applications, such as pathological analysis in immunofluorescence microscopy, bright spots, which may result in extreme positive pixel value differences, may be relatively more important to represent than dark spots, which may result in extreme negative pixel value differences. Accordingly, in some embodiments, the magnitude of the extreme negative pixel difference threshold may be more than the magnitude of the extreme positive pixel difference threshold. For example, in some embodiments, a magnitude of the extreme negative pixel difference threshold may be about four times greater than a magnitude of the extreme positive pixel difference threshold. For example, in some embodiments, the extreme negative pixel difference threshold may have a magnitude of 20, and the extreme positive pixel difference threshold may have a magnitude of 5.

In some embodiments, for pathological analysis, bright spots may be relatively less important to represent than dark spots and so the magnitude of the extreme negative pixel difference threshold may be less than the magnitude of the extreme positive pixel difference threshold.

In some embodiments, the extreme negative pixel difference threshold and the extreme positive pixel difference threshold may have been previously set by a user and stored in the location 452 of the storage memory 404. In various embodiments, block 508 may direct the preparer processor 400 to determine that the first set of image properties may meet the first image property criteria if the extreme positive pixel value difference is less than the extreme positive pixel difference threshold and the extreme negative pixel value difference is less in magnitude than the extreme negative pixel difference threshold.

In various embodiments, using the extreme positive pixel value difference and the extreme negative pixel value difference with different threshold values applied to each may facilitate improved performance in pathology image analysis where bright and dark spots may have different importance for pathological analysis.

In various embodiments, the pixel value differences compared to pixel difference thresholds may be the direct, unscaled (absolute or non-absolute) pixel value differences discussed above. Using such unscaled pixel value differences may be particularly advantageous when processing brightfield microscopy images, for example.

In various embodiments, the pixel value differences may be scaled or determined relative to the overall brightness of the image region (or the entire image). For example, in some embodiments, block 544 of the flowchart 540 shown in FIG. 7 may include code for directing the preparer processor 400 to scale the pixel value differences by a pixel value scaling factor, the pixel value scaling factor representing an overall pixel value intensity of the first representation. In various embodiments, block 544 may direct the preparer processor 400 to thus generate scaled pixel value differences and to treat the scaled pixel value differences generally as set out above having regard to the pixel value differences.

In some embodiments block 544 may direct the preparer processor 400 to determine the scaled or relative pixel value differences $d_r = d_u / \max(\mu, \varepsilon)$, where $d_u$ is the corresponding unscaled pixel value difference and $\max(\mu, \varepsilon)$ acts as a pixel value scaling factor wherein $\mu$ is an overall average pixel value intensity of the first representation, and $\varepsilon$ is a small constant used to prevent division by zero (for example, 0.1) In some embodiments, using relative or scaled pixel value differences may facilitate improved determination of when a second representation can be used in place of a first representation. For example, in some embodiments, using relative or scaled pixel value differences may be particularly advantageous when processing immunofluorescence microscopy images, for example. In various embodiments, this may be the case because in immunofluorescence imaging, a pixel value difference between 0 and 20 may be relatively more important than a pixel value difference between 10000 and 10020, for example. In some embodiments, a similar effect may be provided by scaling one or more pixel difference thresholds.

In various embodiments, block 546 may direct the preparer processor 400 to determine a maximum (in absolute terms) scaled pixel value difference. In some embodiments, block 508 may direct the preparer processor 400 to compare the maximum scaled pixel value difference with a scaled pixel difference threshold. In various embodiments, the scaled pixel difference threshold may differ from the first maximum pixel difference threshold and block 508 may direct the preparer processor 400 to also compare the maximum (unscaled) pixel value difference with the first maximum pixel difference threshold. Accordingly, in some embodiments the preparer processor 400 may not need to know if the image has been captured using brightfield or immunofluorescence microscopy: instead, each kind of difference value may represent a separate image property that may be compared to corresponding image property criteria. In various embodiments, percentile-based values can be used to represent the maximum scaled pixel value differences. In various embodiments, percentile-based values combined with scaling may be used to represent the maximum scaled pixel value differences.

In some embodiments, block 508 may direct the preparer processor 400 to apply additional and/or alternative tests or criteria to determine whether the first set of image properties meets the first image property criteria. For example, in some embodiments block 508 may direct the preparer processor 400 to determine an aggregate representation of the pixel value differences stored in the location 448 and block 508 may direct the preparer processor 400 to determine whether the aggregate representation of the pixel value differences is less than an aggregate threshold. For example, in some embodiments, the aggregate representation may include an average, or another aggregate representation of the absolute values of the pixel value differences. In some embodiments, using an aggregate representation and an associated aggregate threshold may be computationally less intensive than using other image properties for analysis. For example, in some embodiments, the computation of some image properties, such as the percentile-based values, for example, may be relatively computationally intensive. In some embodiments, the aggregate representation may be determined and analyzed before determining and analyzing other computationally intensive image properties and thus using the aggregate representation may facilitate avoiding or skipping computation of such image properties, when the result of the analysis of the aggregate representation is conclusive (e.g., the first representation is determined to not be replaceable by the second representation based on the aggregate representation). Thus, in some embodiments, providing an aggregate representation and an associated analysis may provide a shortcut, which may facilitate an overall higher efficiency or processing speed. In some embodiments, block 508 may direct the preparer processor 400 to determine the aggregate representation as the average value of the absolute values of the pixel value differences. In various embodiments, block 508 may direct the preparer processor 400 to determine the aggregate representation as the root mean square value of the pixel value differences. In some embodiments, block 508 may direct the preparer processor 400 to calculate (non-root) mean square values, or sum-of-squares values, and compare them to a corresponding aggregate threshold (e.g., in case of mean square values, the square of the threshold that would be compared to root mean square values). In various embodiments, this may be faster to calculate than a calculation requiring a root calculation.

In various embodiments, the aggregate threshold may have been previously provided and stored in the storage memory 404 for example. In some embodiments, such as, for example, where the average value of the absolute values acts as the aggregate representation, the aggregate threshold may be 4.0, for example. In some embodiments, a suitable aggregate threshold may be determined empirically depending on the application. In some embodiments, the threshold may decrease as a function of the zoom level (so that the threshold is effectively lower when considering the third representation, than when considering the second representation).

In some embodiments, if the aggregate representation of the pixel value differences stored in the location 448 is not less than the aggregate threshold, then block 508 may direct the preparer processor 400 to determine that the first set of image properties do not meet the first image property criteria and direct the preparer processor 400 to proceed to block 504. In some embodiments, determining whether the aggregate representation is less than the aggregate threshold before applying other tests, such as those based on percentiles, may be advantageous in optimizing the performance of the image preparer 12 determining whether to use a second representation in place of a first representation, for example (because in some embodiments calculating an aggregate representation may be faster than other calculations such as, for example, calculating the percentile values).

In some embodiments, first level image regions, such as the first level image region 200, for example, may be split into more than one zone. In some embodiments, the first level image region 200 may include five zones, for example: a left side, a top side, a right side, a bottom side, and a center. In various embodiments, the non-center zones may be relatively narrow. In some embodiments, the smaller dimension (width or height) of the narrow non-center zones may be as low as 1 pixel, for example. In some embodiments, these zones may be mutually exclusive. In various embodiments, the zones may be overlapping. In various embodiments, a pixel difference analysis may be done separately for each zone. In various embodiments, block 506 of flowchart 500 may direct the preparer processor 400 to process each zone in turn (or in parallel), effectively outputting one or more image properties for each zone. In various embodiments, block 508 may direct the preparer processor 400 to compare each of these image properties to corresponding thresholds or criteria and block 508 may direct the preparer processor 400 to determine that the image properties do not meet the image property criteria if the image properties for any of the zones do not meet corresponding image property criteria.

In some embodiments, any or all of the tests or criteria described herein and/or any additional tests may be applied on their own or in combination with any or all of the other tests or criteria described herein using AND logic, for example, to determine whether the first set of image properties meets the first image property criteria. Thus, in some embodiments, a second representation may be used in place of the first representation only if all of the one or more relevant criteria are fulfilled. In some embodiments, this may facilitate improved functionality while erring on the side of caution.

In some embodiments, a single image region may include more than one channel or layer, with each channel representing a color, for example. In various embodiments, such as in brightfield microscopy, for example, each of the channels may be treated generally as described above and it may be determined that the first set of image properties may meet the first image property criteria only when channel specific image properties meet channel specific image property criteria for all of the channels included in an image region. In various embodiments, such as in immunofluorescence microscopy, for example, each of the channels may be treated generally as described above but independently, so that the first representation of image region 200 may be discarded for one channel but not discarded for another channel.

In some embodiments, block 506 of the flowchart 500 shown in FIG. 6 may include code for directing the preparer processor 400 to input at least the first representation into a machine learning model to cause the machine learning model to generate at least one machine learning model image property. For example, in some embodiments, block 506 of the flowchart 500 shown in FIG. 6 may include code for directing the preparer processor 400 to input the first representation into a convolutional neural network. Therefore, in some embodiments, the at least one machine learning model image property may include at least one neural network image property that is generated by a convolutional neural network.

Figure 12:
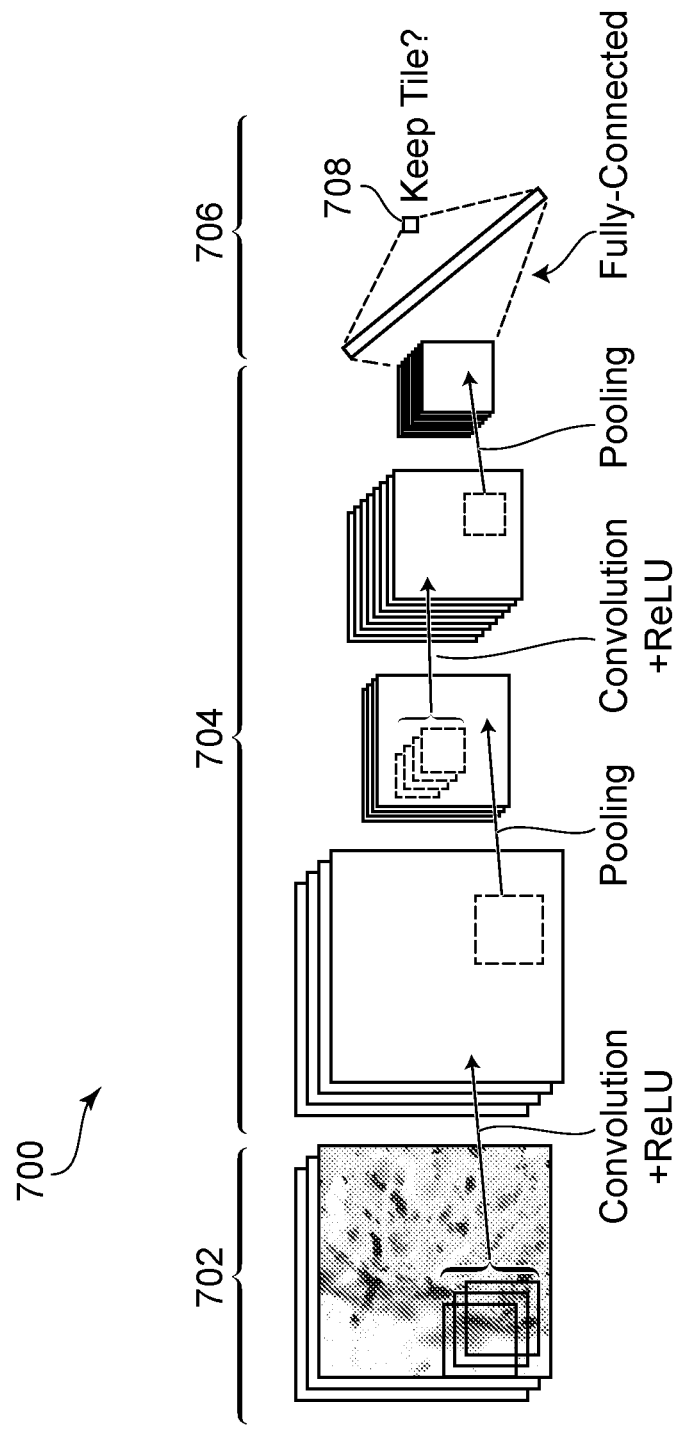
FIG. 12 is a representation of a convolutional neural network that may be used in the system shown in FIG. 1, in accordance with various embodiments.

Referring to FIG. 12, there is shown a representation of a convolutional neural network (CNN) 700 that may be used in execution of the flowchart 500 shown in FIG. 6 in accordance with various embodiments. In some embodiments, block 506 of the flowchart 500 shown in FIG. 6 may include code for directing the preparer processor 400 to input the first representation into the CNN 700 shown in FIG. 12. In various embodiments, data defining the CNN 700 may be stored in the location 466 of the storage memory 404 and so block 506 may direct the preparer processor 400 to retrieve the data defining the CNN 700 from the location 466 of the storage memory 404.

Referring to FIG. 12, the CNN 700 includes an input layer 702, convolution and pooling layers 704, and a multi-layer perceptron layer 706. In various embodiments, the input layer 702 may be configured to receive a first representation of the pathology image 120 which may represent one of the first level image regions 200-258 shown in FIG. 3. In various embodiments, the convolution and pooling layers 704 may include a first convolution and ReLU layer, which may apply a 3×3 filter, a first pooling layer having a pooling size of 2×2, a second convolution and ReLU layer, which may apply a 3×3 filter, and a second pooling layer having a pooling size of 2×2. In various embodiments, the CNN 700 may have a residual neural network (ResNet) structure, for example. In some embodiments, the CNN 700 may have a ResNet-34 structure, for example. In some embodiments, each layer of the multi-layer perceptron layer 706 may include 100 nodes, for example. In some embodiments, the CNN 700 may use, in place of ReLU, a continuously differentiable activation function, such as, for example, Swish or Mish.

In various embodiments, for example, the CNN 700 may have been previously trained to answer the question whether the first level image file representing the first level image region 200 fed to it can be replaced by a corresponding portion of the second level image file representing the second level image region 280 that represents the same image region 200. In various embodiments, the image preparer 12 may be configured to execute blocks of code generally similar to the blocks of code included in the flowchart 500 but with block 506 including code directing the preparer processor 400 to feed the first level image file to the CNN 700. In some embodiments, an output 708 of the CNN 700 may be a scalar value, for example, which may represent a confidence level that a portion of a second level image file may be used in place of the first level image file. In various embodiments, the output 708 may act as a neural network image property.

In some embodiments, block 506 may direct the preparer processor 400 to store the scalar value from the output 708 in the location 468 of the storage memory 404. In various embodiments, the first set of image properties may include the scalar value. In various embodiments, block 508 may direct the preparer processor 400 to determine whether the scalar value stored in the storage memory 404 is less than a CNN output threshold value to determine whether the first set of image properties meets the first image property criteria. In some embodiments, the CNN output threshold value may have been previously provided and stored in the location 469 of the storage memory 404. For example, in some embodiments, the CNN output threshold value may be 0.5, for example.

In some embodiments, the CNN 700 may have been previously trained using sample first level image regions that have been classified (e.g., manually by a person and/or machine assisted person) as "should be kept" (e.g., value 0) or "can be replaced" (e.g., value 1). In various embodiments, a training algorithm such as gradient descent may be used for training. In some embodiments, a loss function such as cross-entropy may be used.

In various embodiments, using a machine learning model such as the CNN 700 to determine a confidence that the second representation should be used in place of the first representation may facilitate improved accuracy and/or expressiveness in the determination of whether to use the second representation in place of the first representation with various differing types of pathological images. In various embodiments using a convolutional neural network as the machine learning model may facilitate high accuracy and/or expressiveness in the determination for pathology images.

In some embodiments, the blocks of code 502-510 of the flowchart 500 shown in FIG. 6 may be executed when pathology images are initially loaded to the image source 14. For example, in some embodiments, pathology images may be loaded and processed using the blocks 502-510 of the flowchart 500 automatically when slides are scanned, or a user may manually cause the pathology images to be processed using the blocks of code 502-510 of the flowchart 500. In some embodiments, the user may cause a batch of pathology images to be processed using the blocks of code 502-510 of the flowchart 500 at the same time, or the user may cause only one pathology image to be processed at a time. In various embodiments blocks 502-510 of the flowchart 500 may be re-executed for one or more pathology images, if the user changes any of the threshold values, for example.

In some embodiments, the blocks of code 502-510 of the flowchart 500 shown in FIG. 6 may be executed in real time in response to a request to display a particular first level image region, instead of in advance.

In some embodiments, the flowchart 580 may be executed by a display device that is separate from the image preparer 12, but which is in communication with the image source 14 and/or the image preparer 12.

In some embodiments, use of the second or third representation in place of the first representation may involve processing steps in addition to or in alternative to displaying. For example, in some embodiments, use of the second or third representation in place of the first representation may involve inputting the second or third representation into a model or function, such as a machine learning model, for pathological analysis.

In some embodiments, the image preparer 12 may be configured to generate the pathology image data including the plurality of representations based on a single pathology image.

In various embodiments, the execution path including the blocks 504-510 may be processed in parallel for the separate image regions of the same pathology image. In such embodiments, each parallel processing unit (which may all be included in the image preparer 12 and implemented using the preparer processor 400, for example) may have its own copies of any or all of the memory locations 442-464 used during execution of the blocks 504-510.

In various embodiments, block 510 of the flowchart 500 shown in FIG. 6 may cause the second representation to be used in place of the first representation using additional or alternative steps to those described above. For example, in some embodiments, block 510 may direct the preparer processor 400 to produce signals identifying the first representation as replaceable by the second representation. In some embodiments, block 510 may direct the preparer processor 400 to generate or update a replaceable first representation record or list stored in the location 470 to include an identifier of the first representation. In various embodiments, the replaceable first representation record may indicate which of the first representations were chosen to be replaced by the corresponding portions of second representations. In some embodiments, the replaceable first representation record may include an identifying image, such as a binary image that indicates which first representations were chosen to be replaced by the corresponding portions of second representations. In various embodiments, block 510 of the flowchart 500 shown in FIG. 6 may direct the preparer processor 400 to update the binary image such that the binary image indicates that the subject image region represented by the first representation was chosen to be replaced by the corresponding portion of the second representation.

In various embodiments, using an identifying image may facilitate ease of identifying the first representations for which a second representation is to be used in place of. In various embodiments, using a binary image may facilitate such identification with a simple and efficient data structure.

In some embodiments, in the binary image, one pixel may correspond to one of the image regions from the corresponding zoom level, for example, the first level image region 200. In some embodiments, a white pixel may represent an image region for which the representation thereof can be replaced and/or the representation has been deleted, and a black pixel may represent an image region for which the representation thereof should not be replaced and/or has not been deleted. In various embodiments, the binary images may be lossless-compressed efficiently, and so using the binary image as the replaceable first representation record may facilitate efficient storage of the replaceable first representation record. In various embodiments, the replaceable first representation record or binary image may be sent to the image source 14 once all image regions in the pathology image 120 shown in FIG. 2 have been considered during execution of the flowchart 500 shown in FIG. 6.

In various embodiments, block 582 of the flowchart 580 shown in FIG. 8 may direct the preparer processor 400 to read the replaceable first representation records or binary images to determine whether the second representation should be provided in place of the first representation. In various embodiments, block 582 may proceed to block 584 if the second representation should be provided in place of the first representation. In various embodiments, identifying the first representation as replaceable, such as, by using a replaceable first representation record may facilitate improvements in overall system speed and cost-efficiency, when unnecessary requests need not be made, or waited to be fulfilled.

In some embodiments, instead of storing second and/or third level image files in the storage memory 404 shown in FIG. 5, there may be stored data representing "views" to image data, which may act as the second and/or third level image files. For example, in some embodiments, the data representing a view may include a "pointer" to the image (or an "id" of the image), and coordinates of the view rectangle (coordinates $x_1$ (left), $x_2$ (right), $y_1$ (top), and $y_2$ (bottom), for example—or equivalently, $x_1$, $y_1$, width, and height). In some embodiments, storing data representing views may facilitate efficiently storing the image data and may avoid unnecessary copying. In various embodiments, program code may handle the "views" generally as it would handle an image file or a copy (of the quadrant).

In various embodiments, the image source 14 may be configured to store the updated pathology image data while also keeping the original pathology image data associated with the pathology image 120, and the image source 14 may be configured to use either the updated or the original pathology image data for different purposes, depending on if fast data transfer, fast display, and/or fast automatic image analysis is preferred over lossless data representation, for example.

In various embodiments, the pathology image data may include additional representations, such as, for example, a fourth representation, a fifth representation, and/or additional representations. In various embodiments, the fourth representation relative to the third representation and the fifth representation relative to the fourth representation and so on may each be treated generally as described above having regard to the third representation relative to the second representation.

In some embodiments, block 644 may direct the preparer processor 400 to consider a first level image region as the subject image region. In various embodiments, this may result in a portion of the second level image file being removed and/or a portion of the third level image file being used in its place. In some embodiments, block 644 may direct the preparer processor 400 to split the second level image file into portions, each corresponding to a first level image region, for example.

In some embodiments, block 506 of the flowchart 500 shown in FIG. 6 may include code for directing the preparer processor 400 to input both the first and second representation into a convolutional neural network, though in various embodiments, this may be redundant with inputting the first representation in the CNN 700 shown in FIG. 12 if the second representation is derivable from the first representation.

In various embodiments, blocks 646 and 648 of the flowchart 600 shown in FIG. may include code for directing the preparer processor 400 to generate any or all of the image properties and apply any or all of the tests or criteria described above having regard to blocks 506 and 508 of the flowchart 500 shown in FIG. 6, except using second and/or third representations instead of first and/or second representations.

As described above, in some embodiments, the image preparer 12 may be configured to cause a second representation to be used in place of a first representation by generating updated pathology image data that does not include the first representation, but only includes the second representation for at least one image region. However, in various embodiments, the first representation may be kept and stored but not used when displaying the image. In some embodiments, the first representation may be discarded after a preconfigured period has elapsed.

In various embodiments, the image source 14 may include an image capturing device, such as, for example, a camera and/or microscope slide scanner configured to capture pathology images. In some embodiments, the image capturing device may be configured to generate pathology image data representing the pathology image.

While specific embodiments of the present disclosure have been described and illustrated, such embodiments should be considered illustrative of the present disclosure only and not as limiting the present disclosure as construed in accordance with the accompanying claims.

The invention claimed is:

1. A method of facilitating processing of pathology images, the method comprising:
receiving pathology image data representing a pathology image having a plurality of image regions, wherein the pathology image data includes, for each of the plurality of image regions, a respective plurality of representations of the image region including a first representation and a second representation, the second representation having a smaller data size than the first representation;
for each of the plurality of image regions:
determining, based at least in part on the first representation of the image region, a first set of image properties;
determining whether the first set of image properties meets first image property criteria; and
if the first set of image properties meets the first image property criteria, producing signals for causing the second representation to be used in place of the first representation, wherein producing signals for causing the second representation to be used in place of the first representation comprises producing signals identifying the first representation as replaceable by the second representation, wherein producing signals identifying the first representation as replaceable by the second representation comprises including an identifier of the first representation in a replaceable first representation record, wherein the replaceable first representation record includes an identifying image including a binary image.

2. The method of claim 1 wherein the second representation has a pixel width smaller than a pixel width of the first representation and the second representation has a pixel height smaller than a pixel height of the first representation.

3. The method of claim 1 wherein, for each of the plurality of image regions, the first set of image properties represents a difference between the first and second representations of the image region.

4. The method of claim 3 wherein, for each of the plurality of image regions, determining the first set of image properties comprises determining based on at least the first and second representations, a first image difference representing the difference between the first and second representations of the image region.

5. The method of claim 4 wherein, for each of the plurality of image regions:
determining the first image difference comprises:
upscaling the second representation of the image region to generate a first upscaled representation of the image region, the first upscaled representation of the image region having the same pixel dimensions as the first representation of the image region; and
for each pixel position in the first representation and the first upscaled representation, determining a pixel value difference between respective pixels of the first representation and the first upscaled representation;
determining the first image difference comprises determining from the pixel value differences, a first maximum pixel value difference; and
determining whether the first set of image properties meets the first image property criteria comprises comparing the first maximum pixel value difference with a first maximum pixel difference threshold.

6. The method of claim 4 wherein, for each of the plurality of image regions:
determining the first image difference comprises:
upscaling the second representation of the image region to generate a first upscaled representation of the image region, the first upscaled representation of the image region having the same pixel dimensions as the first representation of the image region; and
for each pixel position in the first representation and the first upscaled representation, determining a pixel value difference between respective pixels of the first representation and the first upscaled representation;
determining from the pixel value differences, an extreme negative pixel value difference; and
determining from the pixel value differences, an extreme positive pixel value difference; and
determining whether the first set of image properties meets the first image property criteria comprises:
comparing the extreme negative pixel value difference with an extreme negative pixel difference threshold; and
comparing the extreme positive pixel value difference with an extreme positive pixel difference threshold, the extreme positive pixel difference threshold being different from the extreme negative pixel difference threshold.

7. The method of claim 4 wherein:
for each of the plurality of image regions, determining the first image difference comprises:
upscaling the second representation of the image region to generate a first upscaled representation of the image region, the first upscaled representation of the image region having the same pixel dimensions as the first representation of the image region; and
for each pixel position in the first representation and the first upscaled representation, determining a pixel value difference between respective pixels of the first representation and the first upscaled representation, wherein determining the pixel value difference comprises scaling the pixel value difference by a pixel value scaling factor, the pixel value scaling factor based at least in part on an overall pixel value intensity of the first representation.

8. The method of claim 4 wherein, for each of the plurality of image regions:
determining the first image difference comprises:
upscaling the second representation of the image region to generate a first upscaled representation of the image region, the first upscaled representation of the image region having the same pixel dimensions as the first representation of the image region; and
for each pixel position in the first representation and the first upscaled representation, determining a pixel value difference between respective pixels of the first representation and the first upscaled representation; and
the plurality of representations of the image region includes a third representation, the third representation having a smaller data size than the second representation and wherein determining whether the first set of image properties meets the first image property criteria comprises:
determining, based at least in part on the second representation of the image region, a second set of image properties;

determining whether the second set of image properties meets second image property criteria; and if the second set of image properties meets the second image property criteria, producing signals for causing the third representation to be used in place of the first representation.

9. The method of claim 8 wherein, the pixel value differences are first pixel value differences and wherein, for each of the plurality of image regions:

determining the first image difference comprises determining from the first pixel value differences, a first maximum pixel value difference; and determining whether the first set of image properties meets the first image property criteria comprises comparing the first maximum pixel value difference with a first maximum pixel difference threshold; and wherein, for each of the plurality of image regions, determining the second set of image properties comprises determining based on at least the second and third representations, a second image difference representing a difference between the second and third representations of the image region and wherein, for each of the plurality of image regions, determining the second image difference comprises:

upscaling the third representation of the image region to generate a second upscaled representation of the image region, the second upscaled representation of the image region having the same pixel dimensions as the second representation of the image region;

for each pixel position in the second representation and the second upscaled representation, determining a second pixel value difference between respective pixels of the second representation and the second upscaled representation; and determining from the second pixel value differences, a second maximum pixel value difference; and wherein determining whether the second set of image properties meets the second image property criteria comprises comparing the second maximum pixel value difference with a second maximum pixel difference threshold, wherein the second maximum pixel difference threshold has a lower magnitude than the first maximum pixel difference threshold.

10. The method of claim 1 wherein producing signals for causing the second representation to be used in place of the first representation comprises producing signals for causing the second representation to be displayed by at least one display in place of the first representation.

11. The method of claim 1 further comprising receiving a request for the first representation and wherein producing signals for causing the second representation to be used in place of the first representation comprises producing signals for causing the second representation to be provided in response to the request for the first representation.

12. The method of claim 1 wherein for each of the plurality of image regions, determining the first set of image properties comprises inputting at least the first representation of the image region into a machine learning model to cause the machine learning model to generate at least one machine learning model image property and wherein the machine learning model includes a convolutional neural network.

13. The method of claim 1 comprising, for each of the plurality of image regions, whether the first set of image properties meets or does not meet the first image property criteria, causing the second representation to be stored such that the second representation is configured to be provided when requested.

14. A system for facilitating processing of pathology images, the system comprising at least one processor configured to:

receive pathology image data representing a pathology image having a plurality of image regions, wherein the pathology image data includes, for each of the plurality of image regions, a respective plurality of representations of the image region including a first representation and a second representation, the second representation having a smaller data size than the first representation;

for each of the plurality of image regions:

determine, based at least in part on the first representation of the image region, a first set of image properties; and determine whether the first set of image properties meets first image property criteria; and if the first set of image properties meets the first image property criteria, produce signals for causing the second representation to be used in place of the first representation, wherein producing signals for causing the second representation to be used in place of the first representation comprises producing signals identifying the first representation as replaceable by the second representation, wherein producing signals identifying the first representation as replaceable by the second representation comprises including an identifier of the first representation in a replaceable first representation record, wherein the replaceable first representation record includes an identifying image including a binary image.

15. The system of claim 14 wherein the second representation has a pixel width smaller than a pixel width of the first representation and the second representation has a pixel height smaller than a pixel height of the first representation.

16. The system of claim 14 wherein, for each of the plurality of image regions, the first set of image properties represents a difference between the first and second representations of the image region.

17. The system of claim 16 wherein the at least one processor is configured to, for each of the plurality of image regions, determine, based on at least the first and second representations, a first image difference representing the difference between the first and second representations of the image region.

18. The system of claim 17 wherein the at least one processor is configured to, for each of the plurality of image regions:

upscale the second representation of the image region to generate a first upscaled representation of the image region, the first upscaled representation of the image region having the same pixel dimensions as the first representation of the image region; and for each pixel position in the first representation and the first upscaled representation, determine a pixel value difference between respective pixels of the first representation and the first upscaled representation.

19. The system of claim 18 wherein the at least one processor is configured to, for each of the plurality of image regions:

determine from the pixel value differences, a first maximum pixel value difference; and compare the first maximum pixel value difference with a first maximum pixel difference threshold.

20. The system of claim 19 wherein the at least one processor is configured to, for each of the plurality of image regions:
  determine from the pixel value differences, an extreme negative pixel value difference; and
  determine from the pixel value differences, an extreme positive pixel value difference; and
  compare the extreme negative pixel value difference with an extreme negative pixel difference threshold; and
  compare the extreme positive pixel value difference with an extreme positive pixel difference threshold, the extreme positive pixel difference threshold being different from the extreme negative pixel difference threshold.

21. The system of claim 14 wherein, for each of the plurality of image regions, the plurality of representations of the image region includes a third representation, the third representation having a smaller data size than the second representation and wherein the at least one processor is configured to determine whether the first set of image properties meets the first image property criteria by:
  determining, based at least in part on the second representation of the image region, a second set of image properties;
  determining whether the second set of image properties meets second image property criteria; and
  if the second set of image properties meets the second image property criteria, producing signals for causing the third representation to be used in place of the first representation.

22. A non-transitory computer-readable medium having stored thereon codes that when executed by at least one processor cause the at least one processor to:
  receive pathology image data representing a pathology image having a plurality of image regions, wherein the pathology image data includes, for each of the plurality of image regions, a respective plurality of representations of the image region including a first representation and a second representation, the second representation having a smaller data size than the first representation;
  for each of the plurality of image regions:
    determine, based at least in part on the first representation of the image region, a first set of image properties; and
    determine whether the first set of image properties meets first image property criteria; and
  if the first set of image properties meets the first image property criteria, produce signals for causing the second representation to be used in place of the first representation, wherein producing signals for causing the second representation to be used in place of the first representation comprises producing signals identifying the first representation as replaceable by the second representation, wherein producing signals identifying the first representation as replaceable by the second representation comprises including an identifier of the first representation in a replaceable first representation record, wherein the replaceable first representation record includes an identifying image including a binary image.

23. A system for facilitating processing of pathology images, the system comprising:
  means for receiving pathology image data representing a pathology image having a plurality of image regions, wherein the pathology image data includes, for each of the plurality of image regions, a respective plurality of representations of the image region including a first representation and a second representation, the second representation having a smaller data size than the first representation;
  means for, for each of the plurality of image regions:
    determining, based at least in part on the first representation of the image region, a first set of image properties;
    determining whether the first set of image properties meets first image property criteria; and
  means for, if the first set of image properties meets the first image property criteria, producing signals for causing the second representation to be used in place of the first representation, wherein the means for producing signals for causing the second representation to be used in place of the first representation comprises means for producing signals identifying the first representation as replaceable by the second representation, wherein the means for producing signals identifying the first representation as replaceable by the second representation comprises means for including an identifier of the first representation in a replaceable first representation record, wherein the replaceable first representation record includes an identifying image including a binary image.

* * * * *